US008871479B2

(12) United States Patent
Fierobe et al.

(10) Patent No.: US 8,871,479 B2
(45) Date of Patent: *Oct. 28, 2014

(54) CELLULASE CEL5H RELATED REAGENTS AND THEIR USE IN MICROORGANISMS

(75) Inventors: Henri-Pierre Fierobe, Marseilles (FR); Angélique Chanal-Vial, Marseilles (FR); Anne-Laure Molinier, Marseilles (FR); Chantal Tardif, Gemenos (FR); Luc Dedieu, Marseilles (FR)

(73) Assignees: Total Marketing Services, Puteaux (FR); Le Centre National de Recherche Scientifiques (CNRS), Paris (FR); L'Institut National des Sciences Appliquees (INSA), Toulouse (FR); Universite d'Aix-Marseille, Marseille (FR)

( * ) Notice: Subject to any disclaimer, the term of this patent is extended or adjusted under 35 U.S.C. 154(b) by 80 days.

This patent is subject to a terminal disclaimer.

(21) Appl. No.: 13/131,478

(22) PCT Filed: Nov. 26, 2009

(86) PCT No.: PCT/EP2009/065922
§ 371 (c)(1),
(2), (4) Date: Aug. 17, 2011

(87) PCT Pub. No.: WO2010/060964
PCT Pub. Date: Jun. 3, 2010

(65) Prior Publication Data
US 2012/0122176 A1  May 17, 2012

(30) Foreign Application Priority Data
Nov. 28, 2008  (EP) .................... 08291120

(51) Int. Cl.
| C12P 1/04 | (2006.01) |
| C12N 1/20 | (2006.01) |
| C12P 1/00 | (2006.01) |
| C08B 37/00 | (2006.01) |
| C12N 9/42 | (2006.01) |
| C07H 21/04 | (2006.01) |

(52) U.S. Cl.
CPC ............... *C12N 9/2437* (2013.01); *Y02E 50/17* (2013.01); *C12Y 302/01091* (2013.01); *Y02E 50/16* (2013.01)
USPC ........ 435/170; 435/252.3; 435/267; 435/274; 435/209; 536/23.2; 536/23.4

(58) Field of Classification Search
USPC .............. 435/170, 252.3, 267, 274, 209; 536/23.2, 23.4
See application file for complete search history.

(56) References Cited

U.S. PATENT DOCUMENTS

2007/0292929 A1   12/2007   Weiner et al.

FOREIGN PATENT DOCUMENTS

| CN | 101688189 | 3/2010 |
| WO | 2007005646 | 1/2007 |
| WO | 2008021141 | 2/2008 |
| WO | WO 2008/136997 | 11/2008 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Ezeji et al., Production of acetone, butanol and ethanol by *Clostridium beijerinckii* BA101 and in situ recovery by gas stripping. World J. Microbiol. Biotechnol., 2003, vol. 19: 595-603.*
Mistry et al., Production of ethanol by *Clostridium thermosaccharolyticum*: I. Effect of cell recycle and environmental parameters. Biotechnol. Bioeng., 1989, vol. 34: 1295-1304.*
Bhat (2000) Biotechnical Advances 18: 355-383.
Andrykovitch and Marx (1988) Applied Environmental Microbiology 54:3-4.
Taylor et al. (2006) Journal of Bacteriology 188(11): 3849-3861.
Needleman and Wunsch (1970) Journal of Molecular Biology 48: 443-453.
Smith and Waterman (1981) Journal of Molecular Biology 147: 195-197.
Innis et al. (1990) PCR Protocols: A Guide to Methods and Applications, Academic Press.

(Continued)

Primary Examiner — Ganapathirama Raghu
(74) Attorney, Agent, or Firm — Hunton & Williams LLP

(57) ABSTRACT

The invention relates to applications of the cellulase Cel5H of *Saccharophagus degradans* and its homologues, functional fragments and/or variants and engineered forms thereof, in the context of recombinant, more particularly solventogenic microorganisms, more particularly *C. acetobutylicum*. The invention also characterizes a novel domain of the Cel5H cellulase with a putative cellulose-binding module function, and its uses in chimeric proteins for depolymerization of cellulose containing substrates.

14 Claims, 15 Drawing Sheets

(56) References Cited

OTHER PUBLICATIONS

Nakamura et al. (2000) Nucleic Acids Research 28: 292.
Genbank Database Accession No. AAA51444, Oct. 31, 1994.
Genbank Database Accession No. AAC28899, Dec. 5, 2005.
Genbank Database Accession No. AAK78886, Jan. 19, 2006.
Genbank Database Accession No. CAA47637, Oct. 19, 2006.
Genbank Database Accession No. AAV88688, Jan. 25, 2005.
Genbank Database Accession No. CAB02496, Oct. 19, 2006.
Boraston et al. (2004) Biochemical Journal 382: 769-781.
Lytle et al. (2001) Journal of Molecular Biology 307: 745-753.
Adams et al. (2005) Biochemistry 44: 2173-2182.
Bayer et al. (1998) Journal of Structured Biology 124: 221-234.
Fierobe et al. (2002) The Journal of Biological Chemistry 277(51): 49621-49630.
Fierobe et al. (2005) The Journal of Biological Chemistry 280: 16325-16334.
Perret et al. (2004) Journal of Bacteriology 186(1): 253-257.
Mingardon et al. (2007) Applied and Environmental Microbiology 73(22): 7138-7149.
Lynd et al. (2002) Microbiology and Molecular Biology Reviews 66(3): 506-577.
Aoki and Kamei (2006) European Journal of Phycology 41(3): 321-328.
Watson et al. $30^{th}$ Symposium on Biotechnology of Fuels and Chemicals, retrieved from the Internet on Jul. 8, 2009 at: http://sim.confex.com/sim/$30^{th}$/techprogram/P5720.HTM>.
Weiner et al. (2008) Public Library of Science (PLoS) Genetics 4(5): 1-13.
Augustine, Kim et al. (1994) Heterologous Expression of Endo-β-1,4-$_D$-Glucanase from *Clostridium cellulovorans* in *Clostridium acetobutylicum* ATCC 824 following Transformation of the *engB* Gene, Applied and Environmental Micorbiology, American Society for Microbiology, vol. 60, No. 1, pp. 337-340, Jan. 1994.
International Search Report for International Application No. PCT/EP2009/065922, mailed May 25, 2010.
Written Opinion for International Patent Application No. PCT/EP2009/065922, mailed May 25, 2010.
International Preliminary Report on Patentability for International Application No. PCT/EP2009/065922, date of completion: Feb. 21, 2011.

\* cited by examiner

FIG 1A

```
ATGAAATCAGCAACCACAAATCAATCGAGGGCACGCAGTAGCGCCTTTAAAAATAT
GTTGGCGGCATCGCTCGCAGGTTTAGGGCTACTATCAGCTTCTGCATTTGCCGAT
GTAGCCCCGCTAACCGTAGACGGCAATAAAATTCTTAGCGGTGGCCAGCAAGCCA
GTTTTGCCGGTAATAGCTTATTTTGGTCTAACAATGGCTGGGGCGGTGAGAAGTAT
TACACGGCCGGTACCGTTGAATGGCTAAAGCAAGACTGGGGCAGTAATTTAGTTC
GCGCCGCAATGGGTGTCGATGAAAACGGCGGCTACTTAGAAGACCCAGCAGGAA
ACAAAGCGAAAGTAACAACCGTTGTAGATGCAGCCATCGCTAACGATATGTATGTA
ATTATCGATTGGCACAGCCACCACGCCGAAGACTACCAAAACCAAGCCATTAGCT
TTTTCCAAGATATGGCTCGCACCTACGGTAACAACAACAACGTTATATACGAAATT
TATAACGAGCCATTACAGGTTTCTTGGAGCGGCACCATCAAGCCTTACGCAGAAG
CGGTAATTGGCGCAATTCGCGCAATCGACCCAGATAACCTTATTATTGTGGGCAC
GCCTACTTGGTCGCAGGATGTAGACGTAGCCTCGCGCGACCCCATCACGCAGTA
CAGCAACATTGCCTACACTATTCACTTTTATGCGGGCACCCACAAACAATCCCTAC
GCGATAAAGCACAAACCGCATTAAATAATGGTATTGCTTTGTTTGCTACCGAATGG
GGTACAGTAAATGCCAACGGTGACGGCGGTGTAGACGCAGCCGAAACTGATCGT
TGGATGCAGTTTTTTAAAGCGAATCATATAAGCCATGCCAACTGGGCCTTAAACGA
TAAAGCCGAAGGCTCTTCTGCATTAAAGCCTGGCTCTAACGCAAACGGCGGCTGG
AGCAATTCCGACTTAACCGCCTCTGGTACCTATGTTAAAAACTTAATTAAAACATG
GAACGACGGCTCACCGAGCAGCAGCTCATCTAGCAGCACCAGTTCTTCTTCAAGC
AGCTCCTCGTCTAGTAGCTCATCATCTAGCAGCTCTTCATCTAGTAGTTCTGGCGG
TACCAATTTACCCGCGCGCATTGAAGCAGAAAACTACGATAGCGCACCGGTAGAA
ACCACTGCAGGTAATAGCGGCTCACCCACCAATTGTTCGTATAAAGGTATGGGCG
TAGATGTAGAAAACTCTACTGAAGGTGCTTGTAATATTGGCTGGACTGCGGCAGG
CGAAAAAGTAACTTACAACATTGGCAATGCCGATGGCACTTACGATATTGCATTGC
GCGTAGCCTCTATGGATGCGGGCAAACGTATCTCTGTGCATGTAAACAACAGCCT
AGCAGATACCGTAACCACACAAGGTGGCGGCTGGCAGGCATGGACTACCGAAAC
CATTTCTAACGTGTATATCCCATCAAACTCGGTAATTACCGTTGAGTTTTACGATAG
TGGCTCTAACCTAAACTTTTTAAACATTACCGAAAGCTCGGGTACCGAACCACCTG
TAGAACCACCCGTTGAGCCGCCAGTAGAACCACCCGTAGACAACGGTAACTTCCC
ATGTAACGACGGTAACTCTACGCTTGCCAACAACGGCGCCTCCATTAACCTTAAC
CAAGGAGCGTGTGTTAAATACAATCACGGCTGGGGCGATATTCGTTTAGGCACCT
GGAGCGGCAACGGTACCATTCGATACGACGTACTAGACTGCAATAACAACGTAAT
GAGTGATATTGCACAAAAACTTAATGACTTTACTGCTGTAGACACCGCAACAATGA
ACTGCGCACACTACATTTATGTAAAACAAGCCCCTAGCAGCTACAGCCTGCAATTT
GGTAGCTGGTAG (SEQ ID NO : 1)
```

FIG 1B

MKSATTNQSRARSSAFKNMLAASLAGLGLLSASAFADVAPLTVDGNKILSGGQQASF
AGNSLFWSNNGWGGEKYYTAGTVEWLKQDWGSNLVRAAMGVDENGGYLEDPAGN
KAKVTTVVDAAIANDMYVIIDWHSHHAEDYQNQAISFFQDMARTYGNNNNVIYEIYNEP
LQVSWSGTIKPYAEAVIGAIRAIDPDNLIIVGTPTWSQDVDVASRDPITQYSNIAYTIHFY
AGTHKQSLRDKAQTALNNGIALFATEWGTVNANGDGGVDAAETDRWMQFFKANHIS
HANWALNDKAEGSSALKPGSNANGGWSNSDLTASGTYVKNLIKTWNDGSPSSSSSS
STSSSSSSSSSSSSSSSSSSSSSSGGTNLPARIEAENYDSAPVETTAGNSGSPTNCS
YKGMGVDVENSTEGACNIGWTAAGEKVTYNIGNADGTYDIALRVASMDAGKRISVHV
NNSLADTVTTQGGGWQAWTTETISNVYIPSNSVITVEFYDSGSNLNFLNITESSGTEPP
VEPPVEPPVEPPVDNGNFPCNDGNSTLANNGASINLNQGACVKYNHGWGDIRLGTW
SGNGTIRYDVLDCNNNVMSDIAQKLNDFTAVDTATMNCAHYIYVKQAPSSYTLQFGS
W (SEQ ID NO: 2)

FIG 1C

FADVAPLTVDGNKILSGGQQASFAGNSLFWSNNGWGGEKYYTAGTVEWLKQDWGS
NLVRAAMGVDENGGYLEDPAGNKAKVTTVVDAAIANDMYVIIDWHSHHAEDYQNQAI
SFFQDMARTYGNNNNVIYEIYNEPLQVSWSGTIKPYAEAVIGAIRAIDPDNLIIVGTPTW
SQDVDVASRDPITQYSNIAYTIHFYAGTHKQSLRDKAQTALNNGIALFATEWGTVNAN
GDGGVDAAETDRWMQFFKANHISHANWALNDKAEGSSALKPGSNANGGWSNSDLT
ASGTYVKNLIKTWNDGSPSSSSSSSTSSSSSSSSSSSSSSSSSSSSGGTNLPARIE
AENYDSAPVETTAGNSGSPTNCSYKGMGVDVENSTEGACNIGWTAAGEKVTYNIGN
ADGTYDIALRVASMDAGKRISVHVNNSLADTVTTQGGGWQAWTTETISNVYIPSNSVI
TVEFYDSGSNLNFLNITESSGTEPPVEPPVEPPVEPPVDNGNFPCNDGNSTLANNGA
SINLNQGACVKYNHGWGDIRLGTWSGNGTIRYDVLDCNNNVMSDIAQKLNDFTAVDT
ATMNCAHYIYVKQAPSSYTLQFGSW (SEQ ID NO: 3)

FIG 1D

MKHSLHQRFLLPVTLAALSLSASMTNADVAPISTNGNQLLFGGAVDSVAGPSLFWSN
NGWGGEKFYNAGAVASAQQDWNAEIIRAAMGVDEPGGYLEDASANLNRVRAVVDA
AIANDMYVIIDWHSHHAESYTQAAVSFFQQMASEYGQHDNVIYEIYNEPLSVSWSNTI
KPYAEQVIGAIRAVDPDNLIVVGTPTWSQDVDAAANDPITNYNNIAYTLHFYAGTHTQY
LRDKAQYALDMGIPLFVTEWGTVNANGDGGVAYNETNTWMDFLKANNISHANWALN
DKAEGSSALVTGNPSGNWADNQYTASGTFVRDIVRDWSDGDPVDPDPTCTRINMP
GTIEAESFCDMDGIQTESTTDTGGGLNIGWTDAGDWTSYEVNVPAAGRYKVSYRVAA
AQNSGMLQLEAAGGFPTYGSITTPVTGGWQSWQTISHEVDLPAGDQDLAIAVVSGG
WNLNWIKVEPAGGSSSSSSSSSSSSSSSSSSSSTSGCDTANATSITGNTITVSEGQ
CIRYEHTWGSLQLGSWSAAAGTTYDVINCNGQVIADVAQVQNGFSTVATGTNHCNLY
VYVKQAPTSFDLQFGSW (SEQ ID NO: 4)

FIG 1E

DVAPISTNGNQLLFGGAVDSVAGPSLFWSNNGWGGEKFYNAGAVASAQQDWNAEII
RAAMGVDEPGGYLEDASANLNRVRAVVDAAIANDMYVIIDWHSHHAESYTQAAVSFF
QQMASEYGQHDNVIYEIYNEPLSVSWSNTIKPYAEQVIGAIRAVDPDNLIVVGTPTWS
QDVDAAANDPITNYNNIAYTLHFYAGTHTQYLRDKAQYALDMGIPLFVTEWGTVNANG
DGGVAYNETNTWMDFLKANNISHANWALNDKAEGSSALVTGTNPSGNWADNQYTA
SGTFVRDIVRDWSDGDPVDPDPTCTRINMPGTIEAESFCDMDGIQTESTTDTGGGLNI
GWTDAGDWTSYEVNVPAAGRYKVSYRVAAAQNSGMLQLEAAGGFPTYGSITTPVTG
GWQSWQTISHEVDLPAGDQDLAIAVVSGGWNLNWIKVEPAGGSSSSSSSSSSSSSSS
SSSSSSSTSGCDTANATSITGNTITVSEGCCIRYEHTWGSLQLGSWSAAAGTTYDVIN
CNGQVIADVAQVQNGFSTVATGTNHCNLYVYVKQAPTSFDLQFGSW (SEQ ID NO: 5)

FIG 1F

ATGAAAAGTGCAACAACAAATCAAAGTAGAGCAAGAAGTAGTGCATTTAAAAATAT
GCTTGCAGCAAGTTTAGCAGGACTTGGACTTTTAAGTGCAAGTGCATTTGCAGATG
TTGCACCTTTAACAGTTGATGGAAATAAAATACTTAGTGGAGGACAACAGGCATCA
TTTGCAGGAAATAGTTTATTTTGGAGTAATAATGGATGGGGTGGAGAAAAATATTA
TACAGCTGGAACAGTTGAATGGCTTAAACAAGATTGGGGAAGTAATCTTGTTAGAG
CAGCAATGGGAGTTGATGAAAATGGTGGATATTTAGAAGATCCTGCAGGAAATAAA
GCAAAAGTTACAACAGTTGTTGATGCAGCAATAGCAAATGATATGTATGTTATAATA
GATTGGCATAGTCATCATGCAGAAGATTATCAAAATCAAGCAATAAGTTTTTTTCAA
GATATGGCAAGGACTTATGGAAATAATAATAATGTTATATATGAAATATATAATGAA
CCTTTACAGGTTTCATGGTCTGGAACAATAAAACCTTATGCTGAAGCAGTTATAGG
TGCAATAAGAGCAATAGATCCTGATAATCTTATAATAGTTGGAACACCTACATGGT
CTCAAGATGTTGATGTTGCAAGTAGAGATCCTATAACACAATATAGTAATATAGCAT
ATACTATACATTTTTATGCAGGAACACATAAACAAAGTTTAAGAGATAAAGCACAAA
CAGCATTAAATAATGGAATAGCATTATTTGCAACAGAATGGGGAACAGTTAATGCA
AATGGTGATGGTGGAGTTGATGCAGCTGAAACTGATAGATGGATGCAATTTTTTAA
AGCAAATCATATAAGTCATGCAAATTGGGCATTAAATGATAAAGCAGAAGGATCAT
CAGCACTTAAACCTGGAAGTAATGCTAATGGTGGATGGTCAAATAGTGATTTAACA
GCAAGTGGAACTTATGTTAAAAATCTTATAAAAACATGGAATGATGGAAGTCCTAG
TAGTAGTAGTTCAAGTAGTACAAGTAGTTCATCATCAAGTTCAAGTTCATCAAGTAG
TAGTTCTAGTTCAAGTTCTAGTTCTTCTAGTGGAGGAACAAATTTACCTGCAAGAAT
AGAAGCAGAAAATTATGATAGTGCACCTGTTGAAACTACAGCAGGAAATTCAGGAA
GTCCTACAAATTGTAGTTATAAAGGAATGGGAGTAGATGTTGAAAATTCAACAGAA
GGTGCTTGTAATATAGGATGGACAGCAGCTGGAGAAAAAGTTACATATAATATAGG
AAATGCAGATGGAACTTATGATATAGCACTTAGAGTTGCATCAATGGATGCAGGAA
AAAGAATATCAGTTCATGTTAATAATTCATTAGCAGATACAGTTACTACACAAGGTG
GAGGATGGCAAGCATGGACAACAGAAACAATATCAAATGTTTATATACCTAGTAAT
AGTGTTATAACAGTTGAATTTTATGATAGTGGAAGTAATTTAAATTTTCTTAATATAA
CAGAAAGTAGTGGAACAGAACCTCCTGTTGAACCACCAGTAGAACCACCTGTAGA
ACCTCCAGTAGATAATGGAAATTTTCCTTGTAATGATGGAAATTCAACACTTGCAAA
TAATGGTGCAAGTATAAATTTGAATCAAGGTGCATGTGTTAAATATAATCATGGATG
GGGAGATATAAGACTTGGAACATGGTCAGGAAATGGAACAATAAGATATGATGTTC
TTGATTGTAATAATAATGTAATGAGTGATATAGCACAGAAATTAAATGATTTTACAG
CAGTTGATACAGCTACAATGAATTGTGCTCATTATATATATGTAAAACAAGCACCTA
GTAGTTATACACTTCAATTTGGAAGTTGGCATCATCATCACCATCATTAATTAATTA
A (SEQ ID NO: 6)

FIG 1G

MKSATTNQSRARSSAFKNMLAASLAGLGLLSASAFADVAPLTVDGNKILSGGQQASF
AGNSLFWSNNGWGGEKYYTAGTVEWLKQDWGSNLVRAAMGVDENGGYLEDPAGN
KAKVTTVVDAAIANDMYVIIDWHSHHAEDYQNQAISFFQDMARTYGNNNNVIYEIYNEP
LQVSWSGTIKPYAEAVIGAIRAIDPDNLIIVGTPTWSQDVDVASRDPITQYSNIAYTIHFY
AGTHKQSLRDKAQTALNNGIALFATEWGTVNANGDGGVDAAETDRWMQFFKANHIS
HANWALNDKAEGSSALKPGSNANGGWSNSDLTASGTYVKNLIKTWNDGSPSSSSSS
STSSSSSSSSSSSSSSSSSSSSSGGTNLPARIEAENYDSAPVETTAGNSGSPTNCS
YKGMGVDVENSTEGACNIGWTAAGEKVTYNIGNADGTYDIALRVASMDAGKRISVHV
NNSLADTVTTQGGGWQAWTTETISNVYIPSNSVITVEFYDSGSNLNFLNITESSGTEPP
VEPPVEPPVEPPVDNGNFPCNDGNSTLANNGASINLNQGACVKYNHGWGDIRLGTW
SGNGTIRYDVLDCNNNVMSDIAQKLNDFTAVDTATMNCAHYIYVKQAPSSYTLQFGS
WHHHHHH (SEQ ID NO: 7)

SEQUENCE LISTING

```
<160> NUMBER OF SEQ ID NOS: 7

<210> SEQ ID NO 1
<211> LENGTH: 1893
<212> TYPE: DNA
<213> ORGANISM: Saccharophagus degradans strain 2-40

<400> SEQUENCE: 1
atgaaatcag caaccacaaa tcaatcgagg gcacgcagta gcgcctttaa aaatatgttg      60
gcggcatcgc tcgcaggttt agggctacta tcagcttctg catttgccga tgtagcccccg     120 ctaaccgtag acggcaataa aattcttagc ggtggccagc aagccagttt tgccggtaat     180
agcttatttt ggtctaacaa tggctgggc ggtgagaagt attacacggc cggtaccgtt      240
gaatggctaa agcaagactg gggcagtaat ttagttcgcg ccgcaatggg tgtcgatgaa     300
```

```
aacggcggct acttagaaga cccagcagga aacaaagcga aagtaacaac cgttgtagat      360
gcagccatcg ctaacgatat gtatgtaatt atcgattggc acagccacca cgccgaagac      420
taccaaaacc aagccattag cttttttccaa gatatggctc gcacctacgg taacaacaac     480
aacgttatat acgaaattta taacgagcca ttacaggttt cttggagcgg caccatcaag      540
ccttacgcag aagcggtaat tggcgcaatt cgcgcaatcg acccagataa ccttattatt      600
gtgggcacgc ctacttggtc gcaggatgta gacgtagcct cgcgcgaccc catcacgcag      660
tacagcaaca ttgcctacac tattcacttt tatgcgggca cccacaaaca atccctacgc      720
gataaagcac aaaccgcatt aaataatggt attgctttgt ttgctaccga atggggtaca      780
gtaaatgcca acggtgacgg cggtgtagac gcagccgaaa ctgatcgttg gatgcagttt      840
tttaaagcga atcatataag ccatgccaac tgggccttaa acgataaagc cgaaggctct      900
tctgcattaa agcctggctc taacgcaaac ggcggctgga gcaattccga cttaaccgcc      960
tctggtacct atgttaaaaa cttaattaaa acatggaacg acggctcacc gagcagcagc     1020
tcatctagca gcaccagttc ttcttcaagc agctcctcgt ctagtagctc atcatctagc     1080
agctcttcat ctagtagttc tggcggtacc aatttacccg cgcgcattga agcagaaaac     1140
tacgatagcg caccggtaga aaccactgca ggtaatagcg gctcacccac caattgttcg     1200
tataaaggta tgggcgtaga gtagaaaac tctactgaag gtgcttgtaa tattggctgg      1260
actgcggcag gcgaaaaagt aacttacaac attggcaatg ccgatggcac ttacgatatt     1320
gcattgcgcg tagcctctat ggatgcgggc aaacgtatct ctgtgcatgt aaacaacagc     1380
ctagcagata ccgtaaccac acaaggtggc ggctggcagg catggactac cgaaaccatt     1440
tctaacgtgt atatcccatc aaactcggta attaccgttg agttttacga tagtggctct     1500
aacctaaact ttttaaacat taccgaaagc tcgggtaccg aaccacctgt agaaccaccc     1560
gttgagccgc cagtagaacc acccgtagac aacggtaact cccatgtaa cgacggtaac     1620 tctacgcttg ccaacaacgg cgcctccatt aaccttaacc aaggagcgtg tgttaaatac     1680
aatcacggct ggggcgatat tcgtttaggc acctggagcg gcaacggtac cattcgatac     1740
gacgtactag actgcaataa caacgtaatg agtgatattg cacaaaaact taatgacttt     1800
actgctgtag acaccgcaac aatgaactgc gcacactaca tttatgtaaa acaagcccct     1860
agcagctaca ccctgcaatt tggtagctgg tag                                  1893
```

<210> SEQ ID NO 2
<211> LENGTH: 630
<212> TYPE: PRT
<213> ORGANISM: Saccharophagus degradans strain 2-40

<400> SEQUENCE: 2

```
Met Lys Ser Ala Thr Thr Asn Gln Ser Arg Ala Arg Ser Ser Ala Phe
1               5                  10                  15

Lys Asn Met Leu Ala Ala Ser Leu Ala Gly Leu Gly Leu Leu Ser Ala
            20                  25                  30

Ser Ala Phe Ala Asp Val Ala Pro Leu Thr Val Asp Gly Asn Lys Ile
        35                  40                  45

Leu Ser Gly Gly Gln Gln Ala Ser Phe Ala Gly Asn Ser Leu Phe Trp
    50                  55                  60

Ser Asn Asn Gly Trp Gly Gly Glu Lys Tyr Tyr Thr Ala Gly Thr Val
65                  70                  75                  80
```

```
Glu Trp Leu Lys Gln Asp Trp Gly Ser Asn Leu Val Arg Ala Ala Met
                85                  90                  95

Gly Val Asp Glu Asn Gly Gly Tyr Leu Glu Asp Pro Ala Gly Asn Lys
            100                 105                 110

Ala Lys Val Thr Thr Val Val Asp Ala Ala Ile Ala Asn Asp Met Tyr
            115                 120                 125

Val Ile Ile Asp Trp His Ser His His Ala Glu Asp Tyr Gln Asn Gln
            130                 135                 140

Ala Ile Ser Phe Phe Gln Asp Met Ala Arg Thr Tyr Gly Asn Asn Asn
145                 150                 155                 160

Asn Val Ile Tyr Glu Ile Tyr Asn Glu Pro Leu Gln Val Ser Trp Ser
                165                 170                 175

Gly Thr Ile Lys Pro Tyr Ala Glu Ala Val Ile Gly Ala Ile Arg Ala
            180                 185                 190

Ile Asp Pro Asp Asn Leu Ile Ile Val Gly Thr Pro Thr Trp Ser Gln
            195                 200                 205

Asp Val Asp Val Ala Ser Arg Asp Pro Ile Thr Gln Tyr Ser Asn Ile
210                 215                 220

Ala Tyr Thr Ile His Phe Tyr Ala Gly Thr His Lys Gln Ser Leu Arg
225                 230                 235                 240

Asp Lys Ala Gln Thr Ala Leu Asn Asn Gly Ile Ala Leu Phe Ala Thr
            245                 250                 255

Glu Trp Gly Thr Val Asn Ala Asn Gly Asp Gly Val Asp Ala Ala
            260                 265                 270

Glu Thr Asp Arg Trp Met Gln Phe Phe Lys Ala Asn His Ile Ser His
            275                 280                 285

Ala Asn Trp Ala Leu Asn Asp Lys Ala Glu Gly Ser Ser Ala Leu Lys
290                 295                 300

Pro Gly Ser Asn Ala Asn Gly Gly Trp Ser Asn Ser Asp Leu Thr Ala
305                 310                 315                 320

Ser Gly Thr Tyr Val Lys Asn Leu Ile Lys Thr Trp Asn Asp Gly Ser
            325                 330                 335

Pro Ser Ser Ser Ser Ser Ser Thr Ser Ser Ser Ser Ser Ser Ser
            340                 345                 350

Ser Ser Ser Ser Ser Ser Ser Ser Ser Ser Ser Ser Ser Ser Gly
        355                 360                 365

Gly Thr Asn Leu Pro Ala Arg Ile Glu Ala Glu Asn Tyr Asp Ser Ala
            370                 375                 380

Pro Val Glu Thr Thr Ala Gly Asn Ser Gly Ser Pro Thr Asn Cys Ser
385                 390                 395                 400

Tyr Lys Gly Met Gly Val Asp Val Glu Asn Ser Thr Glu Gly Ala Cys
            405                 410                 415

Asn Ile Gly Trp Thr Ala Ala Gly Glu Lys Val Thr Tyr Asn Ile Gly
            420                 425                 430

Asn Ala Asp Gly Thr Tyr Asp Ile Ala Leu Arg Val Ala Ser Met Asp
            435                 440                 445

Ala Gly Lys Arg Ile Ser Val His Val Asn Asn Ser Leu Ala Asp Thr
450                 455                 460

Val Thr Thr Gln Gly Gly Trp Gln Ala Trp Thr Thr Glu Thr Ile
465                 470                 475                 480

Ser Asn Val Tyr Ile Pro Ser Asn Ser Val Ile Thr Val Glu Phe Tyr
            485                 490                 495
```

-continued

```
Asp Ser Gly Ser Asn Leu Asn Phe Leu Asn Ile Thr Glu Ser Ser Gly
                500                 505                 510

Thr Glu Pro Pro Val Glu Pro Val Glu Pro Val Glu Pro Pro
        515                 520                 525

Val Asp Asn Gly Asn Phe Pro Cys Asn Asp Gly Asn Ser Thr Leu Ala
        530                 535                 540

Asn Asn Gly Ala Ser Ile Asn Leu Asn Gln Gly Ala Cys Val Lys Tyr
545                 550                 555                 560

Asn His Gly Trp Gly Asp Ile Arg Leu Gly Thr Trp Ser Gly Asn Gly
                565                 570                 575

Thr Ile Arg Tyr Asp Val Leu Asp Cys Asn Asn Val Met Ser Asp
        580                 585                 590

Ile Ala Gln Lys Leu Asn Asp Phe Thr Ala Val Asp Thr Ala Thr Met
                595                 600                 605

Asn Cys Ala His Tyr Ile Tyr Val Lys Gln Ala Pro Ser Ser Tyr Thr
        610                 615                 620

Leu Gln Phe Gly Ser Trp
625                 630

<210> SEQ ID NO 3
<211> LENGTH: 596
<212> TYPE: PRT
<213> ORGANISM: Saccharophagus degradans strain 2-40

<400> SEQUENCE: 3

Phe Ala Asp Val Ala Pro Leu Thr Val Asp Gly Asn Lys Ile Leu Ser
1               5                   10                  15

Gly Gly Gln Gln Ala Ser Phe Ala Gly Asn Ser Leu Phe Trp Ser Asn
                20                  25                  30

Asn Gly Trp Gly Gly Glu Lys Tyr Tyr Thr Ala Gly Thr Val Glu Trp
            35                  40                  45

Leu Lys Gln Asp Trp Gly Ser Asn Leu Val Arg Ala Ala Met Gly Val
    50                  55                  60

Asp Glu Asn Gly Gly Tyr Leu Glu Asp Pro Ala Gly Asn Lys Ala Lys
65                  70                  75                  80

Val Thr Thr Val Val Asp Ala Ala Ile Ala Asn Asp Met Tyr Val Ile
                85                  90                  95

Ile Asp Trp His Ser His Ala Glu Asp Tyr Gln Asn Gln Ala Ile
            100                 105                 110

Ser Phe Phe Gln Asp Met Ala Arg Thr Tyr Gly Asn Asn Asn Asn Val
        115                 120                 125

Ile Tyr Glu Ile Tyr Asn Glu Pro Leu Gln Val Ser Trp Ser Gly Thr
    130                 135                 140

Ile Lys Pro Tyr Ala Glu Ala Val Ile Gly Ala Ile Arg Ala Ile Asp
145                 150                 155                 160

Pro Asp Asn Leu Ile Ile Val Gly Thr Pro Thr Trp Ser Gln Asp Val
                165                 170                 175

Asp Val Ala Ser Arg Asp Pro Ile Thr Gln Tyr Ser Asn Ile Ala Tyr
            180                 185                 190

Thr Ile His Phe Tyr Ala Gly Thr His Lys Gln Ser Leu Arg Asp Lys
        195                 200                 205

Ala Gln Thr Ala Leu Asn Asn Gly Ile Ala Leu Phe Ala Thr Glu Trp
    210                 215                 220

Gly Thr Val Asn Ala Asn Gly Asp Gly Val Asp Ala Ala Glu Thr
225                 230                 235                 240
```

Asp Arg Trp Met Gln Phe Phe Lys Ala Asn His Ile Ser His Ala Asn
            245                 250                 255

Trp Ala Leu Asn Asp Lys Ala Glu Gly Ser Ser Ala Leu Lys Pro Gly
            260                 265                 270

Ser Asn Ala Asn Gly Gly Trp Ser Asn Ser Asp Leu Thr Ala Ser Gly
            275                 280                 285

Thr Tyr Val Lys Asn Leu Ile Lys Thr Trp Asn Asp Gly Ser Pro Ser
            290                 295                 300

Ser Ser Ser Ser Ser Ser Thr Ser Ser Ser Ser Ser Ser Ser Ser Ser
305                 310                 315                 320

Ser Ser Ser Ser Ser Ser Ser Ser Ser Ser Ser Gly Gly Thr
            325                 330                 335

Asn Leu Pro Ala Arg Ile Glu Ala Glu Asn Tyr Asp Ser Ala Pro Val
            340                 345                 350

Glu Thr Thr Ala Gly Asn Ser Gly Ser Pro Thr Asn Cys Ser Tyr Lys
            355                 360                 365

Gly Met Gly Val Asp Val Glu Asn Ser Thr Glu Gly Ala Cys Asn Ile
            370                 375                 380

Gly Trp Thr Ala Ala Gly Glu Lys Val Thr Tyr Asn Ile Gly Asn Ala
385                 390                 395                 400

Asp Gly Thr Tyr Asp Ile Ala Leu Arg Val Ala Ser Met Asp Ala Gly
            405                 410                 415

Lys Arg Ile Ser Val His Val Asn Asn Ser Leu Ala Asp Thr Val Thr
            420                 425                 430

Thr Gln Gly Gly Gly Trp Gln Ala Trp Thr Thr Glu Thr Ile Ser Asn
            435                 440                 445

Val Tyr Ile Pro Ser Asn Ser Val Ile Thr Val Glu Phe Tyr Asp Ser
            450                 455                 460

Gly Ser Asn Leu Asn Phe Leu Asn Ile Thr Glu Ser Ser Gly Thr Glu
465                 470                 475                 480

Pro Pro Val Glu Pro Pro Val Glu Pro Pro Val Glu Pro Pro Val Asp
            485                 490                 495

Asn Gly Asn Phe Pro Cys Asn Asp Gly Asn Ser Thr Leu Ala Asn Asn
            500                 505                 510

Gly Ala Ser Ile Asn Leu Asn Gln Gly Ala Cys Val Lys Tyr Asn His
            515                 520                 525

Gly Trp Gly Asp Ile Arg Leu Gly Thr Trp Ser Gly Asn Gly Thr Ile
            530                 535                 540

Arg Tyr Asp Val Leu Asp Cys Asn Asn Asn Val Met Ser Asp Ile Ala
545                 550                 555                 560

Gln Lys Leu Asn Asp Phe Thr Ala Val Asp Thr Ala Thr Met Asn Cys
            565                 570                 575

Ala His Tyr Ile Tyr Val Lys Gln Ala Pro Ser Ser Tyr Thr Leu Gln
            580                 585                 590

Phe Gly Ser Trp
            595

<210> SEQ ID NO 4
<211> LENGTH: 585
<212> TYPE: PRT
<213> ORGANISM: Pseudomonas sp. strain ND 137

```
<400> SEQUENCE: 4

Met Lys His Ser Leu His Gln Arg Phe Leu Pro Val Thr Leu Ala
1               5                   10                  15

Ala Leu Ser Leu Ser Ala Ser Met Thr Asn Ala Asp Val Ala Pro Ile
            20                  25                  30

Ser Thr Asn Gly Asn Gln Leu Leu Phe Gly Gly Ala Val Asp Ser Val
        35                  40                  45

Ala Gly Pro Ser Leu Phe Trp Ser Asn Asn Gly Trp Gly Gly Glu Lys
    50                  55                  60

Phe Tyr Asn Ala Gly Ala Val Ala Ser Ala Gln Gln Asp Trp Asn Ala
65                  70                  75                  80

Glu Ile Ile Arg Ala Ala Met Gly Val Asp Glu Pro Gly Gly Tyr Leu
                85                  90                  95

Glu Asp Ala Ser Ala Asn Leu Asn Arg Val Arg Ala Val Val Asp Ala
            100                 105                 110

Ala Ile Ala Asn Asp Met Tyr Val Ile Ile Asp Trp His Ser His His
        115                 120                 125

Ala Glu Ser Tyr Thr Gln Ala Ala Val Ser Phe Phe Gln Gln Met Ala
    130                 135                 140

Ser Glu Tyr Gly Gln His Asp Asn Val Ile Tyr Glu Ile Tyr Asn Glu
145                 150                 155                 160

Pro Leu Ser Val Ser Trp Ser Asn Thr Ile Lys Pro Tyr Ala Glu Gln
                165                 170                 175

Val Ile Gly Ala Ile Arg Ala Val Asp Pro Asp Asn Leu Ile Val Val
            180                 185                 190

Gly Thr Pro Thr Trp Ser Gln Asp Val Asp Ala Ala Asn Asp Pro
        195                 200                 205

Ile Thr Asn Tyr Asn Asn Ile Ala Tyr Thr Leu His Phe Tyr Ala Gly
    210                 215                 220

Thr His Thr Gln Tyr Leu Arg Asp Lys Ala Gln Tyr Ala Leu Asp Met
225                 230                 235                 240

Gly Ile Pro Leu Phe Val Thr Glu Trp Gly Thr Val Asn Ala Asn Gly
                245                 250                 255

Asp Gly Gly Val Ala Tyr Asn Glu Thr Asn Thr Trp Met Asp Phe Leu
            260                 265                 270

Lys Ala Asn Asn Ile Ser His Ala Asn Trp Ala Leu Asn Asp Lys Ala
        275                 280                 285

Glu Gly Ser Ser Ala Leu Val Thr Gly Thr Asn Pro Ser Gly Asn Trp
    290                 295                 300

Ala Asp Asn Gln Tyr Thr Ala Ser Gly Thr Phe Val Arg Asp Ile Val
305                 310                 315                 320

Arg Asp Trp Ser Asp Gly Asp Pro Val Asp Pro Asp Pro Thr Cys Thr
                325                 330                 335

Arg Ile Asn Met Pro Gly Thr Ile Glu Ala Glu Ser Phe Cys Asp Met
            340                 345                 350

Asp Gly Ile Gln Thr Glu Ser Thr Thr Asp Thr Gly Gly Gly Leu Asn
        355                 360                 365

Ile Gly Trp Thr Asp Ala Gly Asp Trp Thr Ser Tyr Glu Val Asn Val
    370                 375                 380

Pro Ala Ala Gly Arg Tyr Lys Val Ser Tyr Arg Val Ala Ala Ala Gln
385                 390                 395                 400

Asn Ser Gly Met Leu Gln Leu Glu Ala Ala Gly Gly Phe Pro Thr Tyr
                405                 410                 415
```

```
Gly Ser Ile Thr Thr Pro Val Thr Gly Gly Trp Gln Ser Trp Gln Thr
            420                 425                 430

Ile Ser His Glu Val Asp Leu Pro Ala Gly Asp Gln Asp Leu Ala Ile
            435                 440                 445

Ala Val Val Ser Gly Gly Trp Asn Leu Asn Trp Ile Lys Val Glu Pro
450                 455                 460

Ala Gly Gly Ser Ser Ser Ser Ser Ser Ser Ser Ser Ser Ser Ser Ser
465                 470                 475                 480

Ser Ser Ser Ser Ser Ser Ser Thr Ser Gly Cys Asp Thr Ala Asn
            485                 490                 495

Ala Thr Ser Ile Thr Gly Asn Thr Ile Thr Val Ser Glu Gly Gln Cys
            500                 505                 510

Ile Arg Tyr Glu His Thr Trp Gly Ser Leu Gln Leu Gly Ser Trp Ser
            515                 520                 525

Ala Ala Ala Gly Thr Thr Tyr Asp Val Ile Asn Cys Asn Gly Gln Val
            530                 535                 540

Ile Ala Asp Val Ala Gln Val Gln Asn Gly Phe Ser Thr Val Ala Thr
545                 550                 555                 560

Gly Thr Asn His Cys Asn Leu Tyr Val Tyr Val Lys Gln Ala Pro Thr
            565                 570                 575

Ser Phe Asp Leu Gln Phe Gly Ser Trp
            580                 585

<210> SEQ ID NO 5
<211> LENGTH: 558
<212> TYPE: PRT
<213> ORGANISM: Pseudomonas sp. strain ND 137

<400> SEQUENCE: 5

Asp Val Ala Pro Ile Ser Thr Asn Gly Asn Gln Leu Leu Phe Gly Gly
1               5                   10                  15

Ala Val Asp Ser Val Ala Gly Pro Ser Leu Phe Trp Ser Asn Asn Gly
            20                  25                  30

Trp Gly Gly Glu Lys Phe Tyr Asn Ala Gly Ala Val Ala Ser Ala Gln
        35                  40                  45

Gln Asp Trp Asn Ala Glu Ile Ile Arg Ala Ala Met Gly Val Asp Glu
    50                  55                  60

Pro Gly Gly Tyr Leu Glu Asp Ala Ser Ala Asn Leu Asn Arg Val Arg
65                  70                  75                  80

Ala Val Val Asp Ala Ala Ile Ala Asn Asp Met Tyr Val Ile Ile Asp
                85                  90                  95

Trp His Ser His His Ala Glu Ser Tyr Thr Gln Ala Ala Val Ser Phe
            100                 105                 110

Phe Gln Gln Met Ala Ser Glu Tyr Gly Gln His Asp Asn Val Ile Tyr
        115                 120                 125

Glu Ile Tyr Asn Glu Pro Leu Ser Val Ser Trp Ser Asn Thr Ile Lys
    130                 135                 140

Pro Tyr Ala Glu Gln Val Ile Gly Ala Ile Arg Ala Val Asp Pro Asp
145                 150                 155                 160

Asn Leu Ile Val Val Gly Thr Pro Thr Trp Ser Gln Asp Val Asp Ala
                165                 170                 175

Ala Ala Asn Asp Pro Ile Thr Asn Tyr Asn Asn Ile Ala Tyr Thr Leu
            180                 185                 190
```

```
His Phe Tyr Ala Gly Thr His Thr Gln Tyr Leu Arg Asp Lys Ala Gln
            195                 200                 205

Tyr Ala Leu Asp Met Gly Ile Pro Leu Phe Val Thr Glu Trp Gly Thr
    210                 215                 220

Val Asn Ala Asn Gly Asp Gly Val Ala Tyr Asn Glu Thr Asn Thr
225                 230                 235                 240

Trp Met Asp Phe Leu Lys Ala Asn Asn Ile Ser His Ala Asn Trp Ala
                245                 250                 255

Leu Asn Asp Lys Ala Glu Gly Ser Ser Ala Leu Val Thr Gly Thr Asn
            260                 265                 270

Pro Ser Gly Asn Trp Ala Asp Asn Gln Tyr Thr Ala Ser Gly Thr Phe
        275                 280                 285

Val Arg Asp Ile Val Arg Asp Trp Ser Asp Gly Asp Pro Val Asp Pro
290                 295                 300

Asp Pro Thr Cys Thr Arg Ile Asn Met Pro Gly Thr Ile Glu Ala Glu
305                 310                 315                 320

Ser Phe Cys Asp Met Asp Gly Ile Gln Thr Glu Ser Thr Thr Asp Thr
                325                 330                 335

Gly Gly Gly Leu Asn Ile Gly Trp Thr Asp Ala Gly Asp Trp Thr Ser
            340                 345                 350

Tyr Glu Val Asn Val Pro Ala Ala Gly Arg Tyr Lys Val Ser Tyr Arg
        355                 360                 365

Val Ala Ala Gln Asn Ser Gly Met Leu Gln Leu Glu Ala Ala Gly
370                 375                 380

Gly Phe Pro Thr Tyr Gly Ser Ile Thr Thr Pro Val Thr Gly Gly Trp
385                 390                 395                 400

Gln Ser Trp Gln Thr Ile Ser His Glu Val Asp Leu Pro Ala Gly Asp
                405                 410                 415

Gln Asp Leu Ala Ile Ala Val Val Ser Gly Gly Trp Asn Leu Asn Trp
            420                 425                 430

Ile Lys Val Glu Pro Ala Gly Gly Ser Ser Ser Ser Ser Ser Ser
        435                 440                 445

Ser Ser Ser Ser Ser Ser Ser Ser Ser Ser Ser Ser Thr Ser Gly
450                 455                 460

Cys Asp Thr Ala Asn Ala Thr Ser Ile Thr Gly Asn Thr Ile Thr Val
465                 470                 475                 480

Ser Glu Gly Gln Cys Ile Arg Tyr Glu His Thr Trp Gly Ser Leu Gln
                485                 490                 495

Leu Gly Ser Trp Ser Ala Ala Gly Thr Thr Tyr Asp Val Ile Asn
            500                 505                 510

Cys Asn Gly Gln Val Ile Ala Asp Val Ala Gln Val Gln Asn Gly Phe
        515                 520                 525

Ser Thr Val Ala Thr Gly Thr Asn His Cys Asn Leu Tyr Val Tyr Val
530                 535                 540

Lys Gln Ala Pro Thr Ser Phe Asp Leu Gln Phe Gly Ser Trp
545                 550                 555

<210> SEQ ID NO 6
<211> LENGTH: 1919
<212> TYPE: DNA
<213> ORGANISM: Saccharophagus degradans strain 2-40

<400> SEQUENCE: 6
atgaaaagtg caacaacaaa tcaaagtaga gcaagaagta gtgcatttaa aaatatgctt        60
```

-continued

```
gcagcaagtt tagcaggact tggactttta agtgcaagtg catttgcaga tgttgcacct      120
ttaacagttg atggaaataa aatacttagt ggaggacaac aggcatcatt tgcaggaaat      180
agtttatttt ggagtaataa tggatggggt ggagaaaaat attatacagc tggaacagtt      240
gaatggctta acaagattg gggaagtaat cttgttagag cagcaatggg agttgatgaa       300
aatggtggat atttagaaga tcctgcagga aataaagcaa aagttacaac agttgttgat     360
gcagcaatag caaatgatat gtatgttata atagattggc atagtcatca tgcagaagat     420
tatcaaaatc aagcaataag ttttttttcaa gatatggcaa ggacttatgg aaataataat    480
aatgttatat atgaaatata taatgaacct ttacaggttt catggtctgg aacaataaaa     540
ccttatgctg aagcagttat aggtgcaata agagcaatag atcctgataa tcttataata     600
gttggaacac ctacatggtc tcaagatgtt gatgttgcaa gtagagatcc tataacacaa     660
tatagtaata tagcatatac tatacatttt tatgcaggaa cacataaaca aagtttaaga     720
gataaagcac aaacagcatt aaataatgga atagcattat ttgcaacaga atggggaaca    780
gttaatgcaa atggtgatgg tggagttgat gcagctgaaa ctgatagatg gatgcaattt    840
tttaaagcaa atcatataag tcatgcaaat tgggcattaa atgataaagc agaaggatca    900
tcagcactta aacctggaag taatgctaat ggtggatggt caaatagtga tttaacagca    960
agtggaactt atgttaaaaa tcttataaaa acatggaatg atggaagtcc tagtagtagt   1020
agttcaagta gtacaagtag ttcatcatca agttcaagtt catcaagtag tagttctagt    1080
tcaagttcta gttcttctag tggaggaaca aatttacctg caagaataga agcagaaaat    1140
tatgatagtc cacctgttga aactacagca ggaaattcag gaagtcctac aaattgtagt    1200
tataaaggaa tgggagtaga tgttgaaaat tcaacagaag gtgcttgtaa tataggatgg    1260
acagcagctg gagaaaaagt tacatataat ataggaaatg cagatggaac ttatgatata    1320
gcacttagag ttgcatcaat ggatgcagga aaaagaatat cagttcatgt taataattca    1380
ttagcagata cagttactac acaaggtgga ggatggcaag catggacaac agaaacaata    1440
tcaaatgttt atatacctag taatagtgtt ataacagttg aattttatga tagtggaagt    1500
aatttaaatt ttcttaatat aacagaaagt agtggaacag aacctcctgt tgaaccacca    1560
gtagaaccac ctgtagaacc tccagtagat aatggaaatt ttccttgtaa tgatggaaat    1620
tcaacacttg caaataatgg tgcaagtata aatttgaatc aaggtgcatg tgttaaatat    1680
aatcatggat ggggagatat aagacttgga acatggtcag gaaatggaac aataagatat    1740
gatgttcttg attgtaataa taatgtaatg agtgatatag cacagaaatt aaatgatttt    1800
acagcagttg atacagctac aatgaattgt gctcattata tatatgtaaa acaagcacct    1860
agtagttata cacttcaatt tggaagttgg catcatcatc accatcatta attaattaa     1919
```

<210> SEQ ID NO 7
<211> LENGTH: 636
<212> TYPE: PRT
<213> ORGANISM: Saccharophagus degradans strain 2-40

<400> SEQUENCE: 7

```
Met Lys Ser Ala Thr Thr Asn Gln Ser Arg Ala Arg Ser Ser Ala Phe
1               5                   10                  15

Lys Asn Met Leu Ala Ala Ser Leu Ala Gly Leu Gly Leu Leu Ser Ala
            20                  25                  30

Ser Ala Phe Ala Asp Val Ala Pro Leu Thr Val Asp Gly Asn Lys Ile
        35                  40                  45
```

-continued

```
Leu Ser Gly Gly Gln Gln Ala Ser Phe Ala Gly Asn Ser Leu Phe Trp
    50              55                  60

Ser Asn Asn Gly Trp Gly Gly Glu Lys Tyr Tyr Thr Ala Gly Thr Val
65              70                  75                  80

Glu Trp Leu Lys Gln Asp Trp Gly Ser Asn Leu Val Arg Ala Ala Met
                85                  90                  95

Gly Val Asp Glu Asn Gly Gly Tyr Leu Glu Asp Pro Ala Gly Asn Lys
                100             105                 110

Ala Lys Val Thr Thr Val Val Asp Ala Ala Ile Ala Asn Asp Met Tyr
            115                 120                 125

Val Ile Ile Asp Trp His Ser His His Ala Glu Asp Tyr Gln Asn Gln
130             135                 140

Ala Ile Ser Phe Phe Gln Asp Met Ala Arg Thr Tyr Gly Asn Asn Asn
145                 150                 155                 160

Asn Val Ile Tyr Glu Ile Tyr Asn Glu Pro Leu Gln Val Ser Trp Ser
                165                 170                 175

Gly Thr Ile Lys Pro Tyr Ala Glu Ala Val Ile Gly Ala Ile Arg Ala
            180                 185                 190

Ile Asp Pro Asp Asn Leu Ile Ile Val Gly Thr Pro Thr Trp Ser Gln
            195                 200                 205

Asp Val Asp Val Ala Ser Arg Asp Pro Ile Thr Gln Tyr Ser Asn Ile
210                 215                 220

Ala Tyr Thr Ile His Phe Tyr Ala Gly Thr His Lys Gln Ser Leu Arg
225                 230                 235                 240

Asp Lys Ala Gln Thr Ala Leu Asn Asn Gly Ile Ala Leu Phe Ala Thr
                245                 250                 255

Glu Trp Gly Thr Val Asn Ala Asn Gly Asp Gly Val Asp Ala Ala
                260                 265                 270

Glu Thr Asp Arg Trp Met Gln Phe Phe Lys Ala Asn His Ile Ser His
            275                 280                 285

Ala Asn Trp Ala Leu Asn Asp Lys Ala Glu Gly Ser Ser Ala Leu Lys
            290                 295                 300

Pro Gly Ser Asn Ala Asn Gly Gly Trp Ser Asn Ser Asp Leu Thr Ala
305                 310                 315                 320

Ser Gly Thr Tyr Val Lys Asn Leu Ile Lys Thr Trp Asn Asp Gly Ser
                325                 330                 335

Pro Ser Ser Ser Ser Ser Ser Thr Ser Ser Ser Ser Ser Ser Ser Ser
                340                 345                 350

Ser Ser Ser Ser Ser Ser Ser Ser Ser Ser Ser Ser Ser Ser Ser Gly
            355                 360                 365

Gly Thr Asn Leu Pro Ala Arg Ile Glu Ala Glu Asn Tyr Asp Ser Ala
            370                 375                 380

Pro Val Glu Thr Thr Ala Gly Asn Ser Gly Ser Pro Thr Asn Cys Ser
385                 390                 395                 400

Tyr Lys Gly Met Gly Val Asp Val Glu Asn Ser Thr Glu Gly Ala Cys
                405                 410                 415

Asn Ile Gly Trp Thr Ala Ala Gly Glu Lys Val Thr Tyr Asn Ile Gly
                420                 425                 430

Asn Ala Asp Gly Thr Tyr Asp Ile Ala Leu Arg Val Ala Ser Met Asp
            435                 440                 445

Ala Gly Lys Arg Ile Ser Val His Val Asn Asn Ser Leu Ala Asp Thr
450                 455                 460
```

```
-continued

Val Thr Thr Gln Gly Gly Gly Trp Gln Ala Trp Thr Thr Glu Thr Ile
465             470                 475                 480

Ser Asn Val Tyr Ile Pro Ser Asn Ser Val Ile Thr Val Glu Phe Tyr
                485                 490                 495

Asp Ser Gly Ser Asn Leu Asn Phe Leu Asn Ile Thr Glu Ser Ser Gly
            500                 505                 510

Thr Glu Pro Pro Val Glu Pro Pro Val Glu Pro Pro Val Glu Pro Pro
        515                 520                 525

Val Asp Asn Gly Asn Phe Pro Cys Asn Asp Gly Asn Ser Thr Leu Ala
    530                 535                 540

Asn Asn Gly Ala Ser Ile Asn Leu Asn Gln Gly Ala Cys Val Lys Tyr
545             550                 555                 560

Asn His Gly Trp Gly Asp Ile Arg Leu Gly Thr Trp Ser Gly Asn Gly
                565                 570                 575

Thr Ile Arg Tyr Asp Val Leu Asp Cys Asn Asn Asn Val Met Ser Asp
            580                 585                 590

Ile Ala Gln Lys Leu Asn Asp Phe Thr Ala Val Asp Thr Ala Thr Met
        595                 600                 605

Asn Cys Ala His Tyr Ile Tyr Val Lys Gln Ala Pro Ser Ser Tyr Thr
        610                 615                 620

Leu Gln Phe Gly Ser Trp His His His His His His
625             630                 635
```

CELLULASE CEL5H RELATED REAGENTS AND THEIR USE IN MICROORGANISMS

CROSS-REFERENCE TO RELATED APPLICATIONS

This is the U.S. National Stage application of International Patent Application No. PCT/EP2009/065922, filed Nov. 26, 2009, which claims priority to EP 08291120.7, filed Nov. 28, 2008, the disclosures of each of which are hereby incorporated by reference in their entirety.

FIELD OF THE INVENTION

The present invention relates to the area of biotechnology and genetic engineering and particularly concerns strategies for utilisation of cellulosic and lignocellulosic materials by means of suitable enzymatic agents and microorganisms expressing such. More specifically, the invention relates to applications of the cellulase Cel5H of *Saccharophagus degradans* and its homologues, functional fragments and/or variants in the context of solventogenic microorganisms, as well as to novel domains and reagents derived from Cel5H and homologues thereof.

BACKGROUND OF THE INVENTION

Cellulosic and lignocellulosic materials are major constituents of plant biomass, and cellulose polymers found therein can provide a significant source of glucose or other fermentable mono- and oligosaccharides that can in turn be metabolised by solventogenic microorganisms to produce useful solvents, such as ethanol, acetone or butanol.

Cellulose polymers can be hydrolysed by cellulose-depolymerising enzymes commonly known as cellulolytic enzymes or cellulases. For example, hydrolysis of native cellulose mainly involves four cellulase types: cellobiohydrolase (1,4-β-D-glucan cellobiohydrolase, EC 3.2.1.91), endo-β-1,4-glucanase (endo-1,4-β-D-glucan 4-glucanohydrolase, EC 3.2.1.4), endo-processive cellulases (EC 3.2.1.4./3.2.1.91), and β-glucosidase (EC 3.2.1.21). Cellulases and related enzymes have been widely utilised in various areas of biotechnology including in food, beer, wine, animal feeds, textile production and laundering, pulp and paper industry, agricultural industry and others (for review see Bhat 2000. Biotechnical Advances 18: 355-383).

Cellulases can vary in their characteristics, such as inter alia they may act as endoglucanases or as processive exoglucanases, they may generate monomers or oligomers of various lengths, they may have contrasting abilities to hydrolyse distinct cellulose forms such as crystalline cellulose, semi-crystalline cellulose, amorphous cellulose or hemicellulose, they may further display different strength of binding to cellulose substrates, different kinetic parameters, etc. Therefore, significant effort needs to be invested into further characterisation of cellulases, so as to identify functional parts or domains thereof which may underlie the interesting properties of these enzymes. Such functional domains can be advantageously combined with other cellulases or domains thereof to generate chimeric enzymes with desired activities.

Further, the recombinant expression of cellulases in solventogenic microorganisms—to allow the production of useful solvents including inter alia ethanol by these microorganisms directly from cellulose-containing materials—is not yet satisfactorily advanced. To achieve further improvements, cellulases particularly suitable for or advantageous in such applications need to be recognised, characterised and selected.

*Saccharophagus degradans* strain 2-40, previously known as *Microbifulber degradans* strain 2-40 and deposited with the American Type Culture Collection under accession number ATCC 43961, is a marine γ-proteobacterium able to degrade at least ten different complex polysaccharides including inter alia cellulose (Andrykovitch & Marx 1988. Appl Environ Microbiol 54: 3-4; Ensor et al. 1999. J Ind Microbiol Biotechnol 23: 123-126).

The *S. degradans* genome has been sequenced and its cellulase system identified, including among many others a cellulase denoted as Cel5H (Taylor et al. 2006. J Bacteriol 188: 3849-61). Further, US2007/0292929 generically contemplates recombinant micro-organisms including ethanologenic bacteria expressing the cellulose degrading proteins from *S. degradans*. However, only the activity of enzymes expressed by *S. degradans* is demonstrated and it is unclear whether any of these enzymes would function appropriately when expressed in ethanologenic bacteria.

SUMMARY OF THE INVENTION

The inventors have performed extensive characterisation of the structure and activity of the Cel5H cellulase of *S. degradans* strain 2-40 and have conclusively determined that Cel5H displays an elevated activity on crystalline cellulose. Therefore, Cel5H is advantageous for heterologous production in solvent-producing (solventogenic) microorganisms, more particularly in ethanologenic microorganisms such as ethanologenic bacteria of *Clostridium* species including *C. acetobutylicum*. Hence, expression (and optionally secretion) of Cel5H in these microorganisms enables their growth on cellulose substrates comprising or enriched in crystalline, semi-crystalline or amorphous cellulose, thereby allowing direct production of useful solvents such as ethanol from cellulose-containing substrates.

Further data generated by the inventors has indicated that Cel5H may act as an exoglucanase or endoprocessive cellulase rather than an endoglucanase as would be expected from its glycoside hydrolase family 5 (GH5) catalytic domain. Also, Cel5H appears to mainly liberate glucose, cellobiose and cellotriose from cellulose. Given the seemingly processive nature of Cel5H and the generation of low complexity cellulose derivatives thereby, its recombinant expression in solventogenic bacteria can be highly advantageous. For example, the products of Cel5H action may either be directly utilised by solventogenic microorganisms or require minimal action by further heterologous cellulase(s), thereby simplifying the design of the recombinant microorganisms and increasing the effectiveness of the process.

The invention integrates the above unexpected realisations in its various aspects.

Hence, an aspect provides a recombinant microorganism expressing the Cel5H polypeptide of *Saccharophagus degradans* strain 2-40 or a homologue thereof, or a functional fragment and/or variant of said Cel5H polypeptide or of said homologue. More particularly, the invention provides such recombinant micro-organisms which are capable of degrading cellulose or cellulose-containing material by said expressed Cel5H polypeptide.

According to particular embodiments the microorganism is a bacterium, more particularly a solventogenic bacterium.

In particular embodiments, the recombinant microorganism comprises a recombinant nucleic acid molecule encoding the Cel5H polypeptide or homologue thereof, or encoding the functional fragment and/or variant of said Cel5H polypeptide or of said homologue, operably linked to regulatory sequences which allow for expression in said microorganism.

In further particular embodiments, the recombinant microorganism produces one or more solvents, fuels and/or chemical intermediates, more particularly solvents chosen from ethanol, acetone, butanol, propionic acid, butyric acid, ether and glycerine.

In further embodiments, the recombinant solventogenic microorganism may produce, or may be engineered to produce, at least or mainly ethanol. The industrial importance of ethanol is rapidly increasing largely due to its utility as an environmentally acceptable fuel. Hence, in an embodiment, the recombinant solventogenic microorganism may be an ethanologenic microorganism.

In particular embodiments, the recombinant microorganism may be a bacterium. In an embodiment, the recombinant solventogenic bacterium may be an ethanologenic bacterium. Alternatively, the recombinant solventogenic microorganism may be yeast, more particularly ethanologenic yeast.

For example, said bacterium may be Gram-positive, such as for example a bacterium of the *Clostridium* species. The invention thus also includes introducing a cellulase originating from a Gram-negative bacterium into a Gram-positive bacterium, which has not been previously suggested. Alternatively, said bacterium may be Gram-negative.

In particular embodiments, the recombinant solventogenic and preferably ethanologenic microorganism is a *Clostridium* species, preferably *Clostridium acetobutylicum*. These bacteria are particularly proficient as solvent- and particularly ethanol-producing bacteria.

In an embodiment, the Cel5H polypeptide or homologue thereof, or the functional fragment and/or variant of said Cel5H polypeptide or of said homologue, may be secreted by said microorganism. So-secreted polypeptides can advantageously act directly on and thereby depolymerise or otherwise interact with or alter cellulose polymers to which the microorganism is exposed. However, embodiments where the polypeptides are expressed intracellularly are also contemplated. For example, so-expressed polypeptides may act on cellulose polymers otherwise internalised by the microorganism or may become released upon lysis of at least a fraction of the microorganisms.

The recombinant microorganism envisaged herein may comprise a recombinant nucleic acid molecule encoding the Cel5H polypeptide or homologue thereof, or encoding the functional fragment and/or variant of said Cel5H polypeptide or of said homologue, operably linked to a secretion signal sequence, optionally combined with one or more additional modules, which allows for secretion in said microorganism, and operably linked to regulatory sequences which allow for expression in said microorganism.

As noted, the invention also teaches homologues of Cel5H and functional fragments and/or variants of said homologues, and their uses in recombinant microorganisms, more particularly solventogenic microorganisms. Preferably, a Cel5H homologue as contemplated herein may comprise a domain homologous to the DZ domain of Cel5H.

Particular embodiments provide the recombinant microorganism as taught herein, wherein said homologue of the Cel5H polypeptide is the ACLA polypeptide of *Pseudomonas* sp. ND137.

Further, as realised by the inventors, the domain structure of the native Cel5H polypeptide can be outlined as GH5-PSL-CBM6-EPR-DZ, wherein GH5 stands for its glycoside hydrolase family 5 domain, PSL for the polyserine linker, CBM6 for carbohydrate-binding module family 6 domain, EPR for the glutamic acid-proline-rich region and, without being limited to this interpretation, DZ represents a C-terminal domain identified by the present inventors as a putative carbohydrate-binding module.

Hence, in particular embodiments the recombinant microorganism as taught herein may express a functional fragment comprising one or more domains chosen from or corresponding to the GH5 domain, the CBM6 domain and the DZ domain of Cel5H. The presence of one or more said domains in the fragment can endow the latter with the functionalities attributed to the respective domains.

The invention further contemplates engineered forms of the Cel5H polypeptide, its homologues, fragments and/or variants, fused to one or more heterologous domains which can supply further functions and activities useful in carbohydrate polymer metabolism, and particularly cellulose metabolism, such as cellulose-depolymerising, cellulose-binding, cellulosome-forming or other activities. Hence, particular embodiments provide recombinant solventogenic microorganisms as taught herein, wherein the Cel5H polypeptide or homologue thereof, or the functional fragment and/or variant of said Cel5H polypeptide or of said homologue, is fused to one or more domains heterologous to the Cel5H polypeptide or homologue thereof, chosen from a glycoside hydrolase (GH) catalytic domain, a carbohydrate-binding module (CBM) domain, a cohesin-binding domain such as a dockerin domain, and a hydrophilic (X module) domain of a cellulosomal scaffoldin protein. Additionally or alternatively, the Cel5H polypeptide or homologue thereof, or the functional fragment and/or variant of said Cel5H polypeptide or of said homologue is fused to a heterologous or its natural signal peptide.

Further, the invention also contemplates advantages of co-expressing the Cel5H or related polypeptides with other polypeptides or enzymes, preferably recombinant polypeptides or enzymes, useful in carbohydrate polymer metabolism, and particularly cellulose metabolism, such as with cellulose-depolymerising, cellulose-binding, cellulosome-forming (such as, e.g., scaffoldin) or other polypeptides. Such co-expression, and optionally and particularly co-secretion, can provide for additive or complementary activities and functions, leading to more efficient depolymerisation and utilisation of cellulose by the present microorganisms.

Further embodiments thus provide recombinant microorganisms as taught herein co-expressing and optionally co-secreting the Cel5H polypeptide or homologue thereof, or the functional fragment and/or variant of said Cel5H polypeptide or of said homologue, with one or more polypeptides (also referred to herein as co-expressed polypeptides), preferably recombinant polypeptides participating in carbohydrate polymer metabolism, and particularly cellulose metabolism, particularly with one or more enzymes capable of degrading lignocellulosic material, more particularly with one or more glycoside hydrolases, even more particularly with one or more cellulases.

In particular embodiments, the catalytic action of said one or more co-expressed polypeptides, such as co-expressed enzymes, more particularly co-expressed cellulases, may be additive or complementary, preferably complementary, to the enzymatic activity of the Cel5H polypeptide or homologue thereof, or the functional fragment and/or variant of said Cel5H polypeptide or of said homologue. By means of example and not limitation, a first cellulase may be considered as having activity complementary to a second cellulase if the first and second cellulases act preferentially on distinct substrates (such as, e.g., crystalline cellulose, semi-crystalline cellulose, amorphous cellulose or hemicellulose), or if the first and second cellulases produce distinct products (e.g., distinct populations of sugar monomers and/or oligomers), or if the first cellulase acts preferentially on reaction products of the second cellulase or vice versa, etc.

In further embodiments, the one or more co-expressed cellulases may be chosen from family-5, 6, 8, 9 and 48 cellulases. In further particular embodiments, the one or more co-expressed cellulases may be chosen from *Clostridium cellulolyticum* cellulases Cel48F, Cel9G, Cel9R, Cel9P, Cel9E, Cel9H, Cel9J, Cel9M, Cel8C, Cel5N and Cel5A, and *Saccharophagus degradans* strain 2-40 cellulases Cel9A, Cel9B, Cel5J, Cel5I, Cel5F, Cel5D, Cel5B, Cel9G, Cel5E, Cel5A, Cel5C and Cel6A, and functional fragments and/or variants of any one of said cellulases.

Further embodiments provide recombinant microorganisms as taught herein, more particularly solventogenic recombinant microorganisms wherein the Cel5H polypeptide or homologue thereof, or the functional fragment and/or variant of said Cel5H polypeptide or of said homologue, and optionally the one or more co-expressed polypeptides, more particularly one or more co-expressed cellulases as taught above, are comprised in a hybrid and/or covalent cellulosome or minicellulosome (both encompassed throughout this specification by the generic reference to cellulosome). Cellulosomes can provide for supra-molecular organisation of inter alia cellulose-binding and cellulose-depolymerising activities, thereby achieving greater efficiency of carbohydrate polymer metabolism, particularly cellulose metabolism.

In a further aspect, the invention provides methods for the degradation of a substance comprising cellulose, such as lignocellulosic or cellulosic material or biomass, comprising contacting said substance with the recombinant microorganism as taught herein. In particular embodiments, the substance comprises or is enriched for crystalline cellulose.

A related aspect provides methods for producing a solvent, fuel or chemical intermediate from a substance comprising cellulose, such as lignocellulosic or cellulosic material or biomass, comprising treating said substance with one or more of the microorganisms as taught herein. In particular embodiments, the substance comprises or is enriched for crystalline cellulose. In most particular embodiments, the solvent is ethanol and the microorganism is an ethanologenic microorganism.

In particular embodiments, the methods of the invention comprises growing recombinant microorganisms as described herein on cellulose substrates comprising or enriched in crystalline, semi-crystalline or amorphous cellulose, thus ensuring direct production of useful solvents such as ethanol from cellulose-containing substrates.

It shall also be appreciated that while in the foregoing aspects and embodiments the invention has been disclosed primarily in connection with the recombinant microorganisms, the invention also encompasses aspects relating to recombinant means and reagents useful for obtaining the recombinant microorganisms, methods for obtaining the recombinant microorganisms using such recombinant means and reagents, methods for expressing the desired polypeptides in the recombinant microorganisms, as well as to the expressed polypeptides and combinations thereof per se and methods for preparation thereof.

Accordingly, a further aspect provides isolated Cel5H polypeptides of *Saccharophagus degradans* strain 2-40 or a homologue thereof, or a functional fragment and/or variant of said Cel5H polypeptide or of said homologue. Another aspect provides recombinant nucleic acid molecules encoding the Cel5H polypeptide or homologue thereof, or encoding the functional fragment and/or variant of said Cel5H polypeptide or of said homologue.

Further embodiments of this aspect of the invention provide recombinant nucleic acid molecules encoding the Cel5H polypeptide or homologue thereof, or encoding the functional fragment and/or variant of said Cel5H polypeptide or of said homologue, operably linked to regulatory sequences which allow for expression in a host microorganism of interest. In particular embodiments, said host is a solventogenic microorganism. In more particular embodiments, said host is an ethanologenic microorganism as taught elsewhere in this specification. In particular embodiments of the recombinant nucleic acid molecules provided herein, the nucleic acid sequence encoding the Cel5H polypeptide or homologue thereof, or encoding the functional fragment and/or variant of said Cel5H polypeptide or of said homologue, is adapted to a host micro-organism codon bias, Further embodiments provide recombinant nucleic acid molecules encoding the Cel5H polypeptide or homologue thereof, or encoding the functional fragment and/or variant of said Cel5H polypeptide or of said homologue, operably linked to a secretion signal sequence which allows for secretion in a host microorganism of interest, particularly in a recombinant microorganism, more particularly in a solventogenic and more preferably ethanologenic microorganism as taught elsewhere in this specification.

Further embodiments provide recombinant nucleic acid molecules encoding the Cel5H polypeptide or homologue thereof, or encoding the functional fragment and/or variant of said Cel5H polypeptide or of said homologue, operably linked to a secretion signal sequence which allows for secretion in a host microorganism of interest, and operably linked to regulatory sequences which allow for expression in the host microorganism of interest, particularly in a solventogenic and more particularly in an ethanologenic microorganism as taught elsewhere in this specification.

A further aspect is a vector, such as for instance a cloning vector, a shuttle vector and/or an expression vector, comprising one or more of the recombinant nucleic acids as disclosed above.

A further aspect provides host microorganisms of interest transformed with one or more of the recombinant nucleic acids or with a vector as described above. In an embodiment, the microorganism may be a bacterium, more particularly a bacterium chosen from *Escherichia coli, Salmonella tymphimurium, Serratia marcescens, Salmonella typhimurium* and *Bacillus subtilis*. Such bacteria are particularly suitable for overproduction of recombinant polypeptides, for example for purposes of purification. In particular embodiments, the host microorganism is a solventogenic and preferably an ethanologenic microorganism as taught elsewhere in this specification. A further aspect provides a cell lysate or cell extract directly obtained or obtainable from so-transformed microorganisms.

Hence, also provided are methods for obtaining recombinant microorganisms according to the invention, preferably solventogenic and more preferably ethanologenic microorganisms as taught elsewhere in this specification, comprising transforming a host microorganism with a recombinant nucleic acid or vector as taught herein.

Further provided are methods for production, and optionally and most particularly secretion, of one or more Cel5H polypeptides or homologues thereof, or functional fragments and/or variants of said Cel5H polypeptides or of said homologues, comprising transforming a host microorganism with one or more of the respective recombinant nucleic acids or vectors as taught herein, and culturing or maintaining the so-transformed microorganisms under conditions effective to cause expression of the respective polypeptides. Advantageously, the respective polypeptides are produced in a biologically active form. Optionally, the methods may comprise a step of isolating the respective polypeptides.

Hence, also contemplated is the use of the recombinant nucleic acids, vectors or host cells as disclosed herein for the production, and optionally and particularly secretion of Cel5H polypeptide or homologue thereof, or functional fragment and/or variant of said Cel5H polypeptide or of said homologue. Preferably, the respective polypeptides are produced in a biologically active form.

In particular embodiments of the above polypeptides, recombinant nucleic acids, vectors, transformed host microorganisms, methods and uses are characterized by one or more of the following features:

the Cel5H homologue comprises a domain homologous to the DZ domain of Cel5H; and/or the Cel5H homologue is the ACLA polypeptide of *Pseudomonas* sp. ND137; and/or the functional fragment comprises one or more domains chosen from or corresponding to the GH5 domain, the CBM6 domain and the DZ domain of Cel5H; and/or the one or more Cel5H polypeptides or homologues thereof, or the functional fragments and/or variants of the one or more Cel5H polypeptides or said homologue, is fused to one or more domains heterologous to the Cel5H polypeptide or homologue thereof, chosen from a GH catalytic domain, a CBM domain, a cohesin-binding domain such as a dockerin domain, and an X module domain of a cellulosomal scaffoldin protein; and/or the one or more Cel5H polypeptides or homologues thereof, or the functional fragment and/or variant of said one or more Cel5H polypeptides or of said homologues, may be co-expressed and optionally co-secreted with one or more polypeptides, preferably recombinant polypeptides or enzymes, participating in carbohydrate polymer metabolism, particularly cellulose metabolism, preferably with one or more enzymes capable of degrading lignocellulosic material, more preferably with one or more heterologous cellulases as taught herein; and/or the one or more Cel5H polypeptides or homologues thereof, or the functional fragment and/or variant of said Cel5H polypeptides or of said homologues, and optionally the one or more co-expressed polypeptides, more particularly co-expressed cellulases, as taught above, are comprised in a hybrid and/or covalent cellulosome.

Hence, an aspect provides isolated compositions comprising the Cel5H polypeptide or a homologue thereof, or a functional fragment and/or variant of said Cel5H polypeptide or of said homologue, and further comprising one or more polypeptides participating in carbohydrate polymer metabolism, and particularly cellulose metabolism, preferably one or more enzymes capable of degrading lignocellulosic material, more preferably one or more heterologous cellulases as taught herein. In particular embodiments of said composition, the recited components are present as discrete or free polypeptides. In other embodiments, the recited polypeptides are comprised in a hybrid and/or covalent cellulosome.

The inventors have further performed a thorough analysis of the structure and organisation of the Cel5H polypeptide and have identified the presence of a new domain not previously identified as such, near the C-terminal end of the Cel5H polypeptide (termed domain DZ hereafter). Without limitation, the inventor's data suggest a putative carbohydrate-binding module (and/or oligomerisation module function) for the DZ domain and indicate that its presence may be at least partly responsible for the good ability of Cel5H to depolymerise crystalline cellulose. Therefore, it is a further realisation of the invention that the DZ domain or portions of the Cel5H polypeptide comprising the DZ domain can be employed in a variety of enzymatic systems to improve their ability to digest and degrade crystalline cellulose.

Accordingly, a further aspect is an isolated domain (DZ domain) of the Cel5H polypeptide of *Saccharophagus degradans* strain 2-40 from amino acid 496 to amino acid 596 of said Cel5H polypeptide (such as, e.g., in the exemplary, mature Cel5H polypeptide SEQ ID NO: 3 shown in FIG. 1C) or an isolated domain homologous thereto, or a functional fragment and/or variant of said DZ domain or of said homologous domain.

In particular embodiments, a domain homologous to the Cel5H DZ is a domain stretching from amino acid 463 to amino acid 558 of the ACLA polypeptide of *Pseudomonas* sp. ND137 (such as, e.g., in the exemplary, mature ACLA polypeptide SEQ ID NO: 5 shown in FIG. 1E)

Particular embodiments provide for an isolated fragment of the Cel5H polypeptide or of a homologue or variant thereof, having the structure EPR-DZ, CBM6-EPR-DZ or PSL-CBM6-EPR-DZ, wherein EPR, CBM6 and PSL have meanings as explained elsewhere in this specification. Such fragments comprise the DZ domain which provides for its advantageous functions, and optionally, such fragment may include the Cel5H carbohydrate-binding module CBM6 which may further stimulate the ability to degrade crystalline cellulose or hemicellulosic substrates. Moreover, endogenous linker sequences can provide advantageous means for fusing the DZ and optionally CBM6 domains to other polypeptides while retaining their structure and function.

Hence, particular embodiments provide for an isolated fragment of the ACLA polypeptide comprising a domain homologous to the DZ domain of Cel5H.

Further contemplated are uses of the isolated DZ domain or the functional fragment and/or variant thereof, or of the isolated fragment as taught above, as a carbohydrate-binding module. Such use can endow novel carbohydrate- or cellulose-binding properties on various enzyme systems.

Another aspect relates to chimeric polypeptides comprising an isolated DZ domain most particularly of Cel5H or a functional fragment and/or variant thereof, or comprising an isolated fragment of Cel5H comprising the DZ domain, and further comprising one or more domains heterologous to the Cel5H polypeptide or homologue thereof, chosen from a GH catalytic domain, a CBM domain, a cohesin-binding domain such as a dockerin domain, and an X module domain of a cellulosomal scaffoldin protein. Such modular combinations allow the generation of novel cellulose-degrading enzymes with useful activity towards crystalline cellulose or hemicellulosic substrates.

Other aspects provide chimeric polypeptides comprising the isolated DZ domain or the functional fragment and/or variant thereof, or an isolated fragment of Cel5H comprising the DZ domain, fused to one or more polypeptides participating in carbohydrate polymer metabolism, particularly cellulose metabolism, preferably to one or more enzymes capable of degrading lignocellulosic material, more preferably to one or more glycoside hydrolases, even more preferably to one or more cellulases, which is (are) heterologous to the Cel5H polypeptide or homologue thereof. Nevertheless, fusions of additional DZ domain(s) with a Cel5H polypeptide or a homologue thereof, or fragments and/or variants thereof as described herein, are also contemplated.

A further aspect provides recombinant nucleic acid molecules encoding the isolated DZ domain or the isolated domain homologous thereto or the functional fragment and/or variant thereof, or encoding an isolated fragment of Cel5H comprising the DZ domain or homologue thereof, or encoding the chimeric polypeptide as described above.

A particular embodiment of this aspect provides a recombinant nucleic acid molecule encoding the isolated DZ domain or the isolated domain homologous thereto or the functional fragment and/or variant thereof, or encoding the isolated fragment of Cel5H comprising the DZ domain or a homologue thereof, or encoding the chimeric polypeptide as described above, operably linked to regulatory sequences which allow for expression in a host microorganism of interest, preferably in a solventogenic and more preferably in an ethanologenic microorganism as taught elsewhere in this specification.

A further embodiment provides a recombinant nucleic acid molecule encoding the isolated DZ domain or the isolated domain homologous thereto or the functional fragment and/or variant thereof, or encoding the isolated fragment of Cel5H comprising the DZ domain or a homologue thereof, or encoding the chimeric polypeptide as described above, operably linked to a secretion signal sequence which allows for secretion in a host microorganism of interest, preferably in a solventogenic and more preferably in an ethanologenic microorganism as taught elsewhere in this specification.

Yet a further embodiment of this aspect provides a recombinant nucleic acid molecule encoding the isolated DZ domain or the isolated domain homologous thereto or the functional fragment and/or variant thereof, or encoding the isolated fragment of Cel5H comprising the DZ domain or a homologue thereof, or encoding the chimeric polypeptide as described above, operably linked to a secretion signal sequence which allows for secretion in a host microorganism of interest, and operably linked to regulatory sequences which allow for expression in the host microorganism of interest, preferably in a solventogenic and more preferably in an ethanologenic microorganism as taught elsewhere in this specification.

A further aspect provides vectors, such as for instance a cloning vector, a shuttle vector and/or an expression vector, comprising any of the above recombinant nucleic acid molecules.

A further aspect provides a host microorganism of interest transformed with the above described recombinant nucleic acid molecule or vector. In particular embodiments, the microorganism is a bacterium, more preferably a bacterium chosen from *Escherichia coli, Salmonella tymphimurium, Serratia marcescens, Salmonella typhimurium* and *Bacillus subtilis*. In particular embodiments, the microorganism may be a solventogenic and is preferably an ethanologenic microorganism as taught elsewhere in this specification. A further aspect provides a cell lysate or cell extract directly obtained or obtainable from so-transformed microorganisms.

In particular embodiments, the isolated DZ domain or the isolated domain homologous thereto or the functional fragment and/or variant thereof, or the isolated fragment of Cel5H comprising the DZ domain or a homologue thereof, or the chimeric polypeptide as described above, and optionally the one or more co-expressed polypeptides involved in carbohydrate polymer metabolism, particularly cellulose metabolism, may be comprised in a hybrid and/or covalent cellulosome.

In a further aspect, the invention provides methods for the degradation of a substance comprising cellulose, such as lignocellulosic or cellulosic material or biomass, comprising contacting said substance with the isolated DZ domain or the isolated domain homologous thereto or the functional fragment and/or variant thereof, or with the isolated fragment of Cel5H comprising the DZ domain or a homologue thereof, or with the chimeric polypeptide as described above, or with a recombinant microorganism expressing such. In an embodiment, the substance may comprise or be enriched for crystalline cellulose, semi-crystalline cellulose or amorphous cellulose.

A related aspect provides methods for producing a solvent, a fuel or a chemical intermediate from a substance comprising cellulose, such as lignocellulosic or cellulosic material or biomass, comprising treating said substance with the isolated DZ domain or the isolated domain homologous thereto or the functional fragment and/or variant thereof, or with the isolated fragment of Cel5H comprising the DZ domain or a homologue thereof, or with the chimeric polypeptide as described above, or with a recombinant solventogenic microorganism expressing such. In an embodiment, the substance may comprise or be enriched for crystalline cellulose. In particular embodiments methods are provided for producing a solvent, more particularly ethanol and the microorganism may be an ethanologenic microorganism.

A further aspect provides compositions comprising cellulose degradation products and/or solvents, more particularly ethanol, obtained or obtainable by the methods described herein. Such compositions may be crude cultivation media or (at least) partially enriched and/or purified for the product of the Cel5H polypeptide (or homologue or fragment thereof) or partially enriched and/or purified for the solvent, fuel or chemical intermediate. In particular embodiments, such compositions are characterized by the increased glucose, cellobiose and cellotriose content. In further particular embodiments compositions are provided wherein the content of glucose, cellobiose and/or cellotriose is greater than 10 wt %, greater than 20 wt %, greater than 30 wt %, greater than 40 wt %, greater than 50 wt %, greater than 60 wt %, greater than 70 wt %, greater than 80 wt %, greater than 90 wt % or more.

In further particular embodiments, such compositions are characterized by the high content in solvent, fuel or chemical intermediate of interest. In further particular embodiments compositions are provided wherein the content of solvent, fuel or chemical intermediate is greater than 10 wt %, greater than 20 wt %, greater than 30 wt %, greater than 40 wt %, greater than 50 wt %, greater than 60 wt %, greater than 70 wt %, greater than 80 wt %, greater than 90 wt %, greater than 90 wt %, or between 96% and 99.9 wt %. In particular embodiments the concentration of the solvent, fuel or chemical intermediate in the composition is greater than about 10 g/L, and preferably greater than about 15 g/L.

These and other aspects and embodiments of the invention are further explained here below and in the appended claims, as well as illustrated by non-limiting examples.

BRIEF DESCRIPTION OF THE FIGURES

FIG. 1 illustrates exemplary coding nucleic acid sequence (A) and amino acid sequence (B-C) of native Cel5H polypeptide of *Saccharophagus degradans* strain 2-40 containing (B) or not containing (C) the N-terminal secretion signal sequence; exemplary amino acid sequence of native ACLA protein of *Pseudomonas* sp. ND137 containing (D) or not containing (E) the N-terminal secretion signal sequence; exemplary engineered Cel5H-coding nucleic acid sequence (F) and amino acid sequence (G) adapted to *Clostridium acetobutylicum* codon bias and containing 6×His codons or a tag at the 3' (C-term) end.

DETAILED DESCRIPTION OF THE INVENTION

Figure 2:
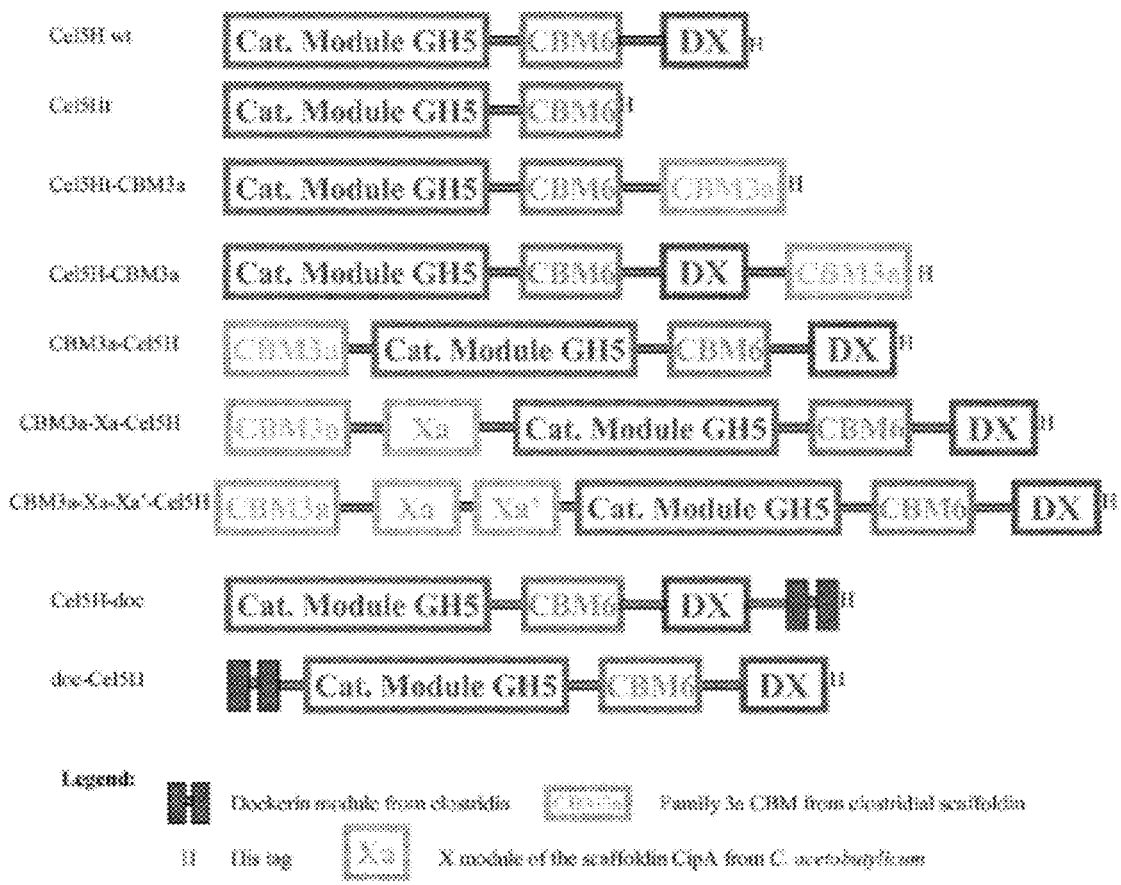
FIG. 2 schematically illustrates various fragments and derivatives of Cel5H that were or are engineered for expression, according to particular embodiments of the invention.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the terms "Cel5H", "Cel5H polypeptide" or "Cel5H protein" refer to the polypeptide or protein of *Saccharophagus degradans* strain 2-40 commonly known under these designations in the art (see in particular Taylor et al. 2006, supra). The above designations particularly refer to such polypeptides with a native sequence, i.e., polypeptides of which the primary sequence is the same as that of the Cel5H protein of *S. degradans* strain 2-40 found in or derived from nature. A skilled person understands that native sequences of Cel5H might differ between different sub-strains or sub-cultures of *S. degradans* strain 2-40 due to genetic divergence or spontaneous mutation(s). The native sequences of Cel5H may further diverge due to post-transcriptional or post-translational modifications. Accordingly, all Cel5H sequences found in or derived from nature are considered "native".

The above designations encompass the Cel5H polypeptide when forming a part of a living organism, microorganism or cells, as well as when at least partly isolated from such sources. The terms also encompass Cel5H polypeptides when produced by recombinant or synthetic means.

The Cel5H polypeptide is normally secretory and may exist in a precursor form comprising a cleavable N-terminal secretion signal sequence, or in a mature form lacking said signal sequence. Depending on context readily understood by a skilled person, a reference herein to the Cel5H polypeptide may encompass said mature form and/or said precursor forms.

Exemplary Cel5H polypeptides include without limitation the polypeptide encoded by the nucleic acid coding sequence as annotated under the NCBI Entrez Gene database (www.ncbi.nlm.nih.gov/sites/entrez?db=gene) locus tag Sde_3237 (GeneID:3965710), and under the NCBI Genbank (www.ncbi.nlm.nih.gov/Genbank/index.html) accession number NC 007912 (sequence version 1, database entry updated 20Jul. 2008), also reproduced in FIG. 1A (SEQ ID NO: 1); and the Cel5H polypeptide as annotated under the NCBI Genbank accession number YP 528706 (sequence version 1, database entry updated 20 Jul. 2008) and the Uniprot/Swissprot (www.expasy.org/) accession number Q21FN5 (sequence version 1 entered on Apr. 18, 2006), as exemplarily reproduced in FIG. 1B (SEQ ID NO: 2).

This sequence corresponds to a Cel5H precursor comprising the signal sequence. An exemplary mature Cel5H polypeptide, i.e., with the signal sequence processed away, is represented by amino acid positions 35 to 630 of said precursor sequence, as exemplarily reproduced in FIG. 1C (SEQ ID NO: 3).

One shall appreciate that the actual cleavage by signal peptidase may potentially occur at a peptide bond nearby the predicted cleavage site between amino acids 34 and 35 of the precursor Cel5H such as shown in FIG. 1B. For example, the actual cleavage might occur at any of the peptide bonds within the amino acid region from position 30 to 40, preferably 31 to 39, more preferably 32 to 38, even more preferably 32 to 37, still more preferably 33 to 36, of the precursor Cel5H such as shown in FIG. 1B.

Further, unless indicated otherwise expressly or by context, whenever domains or other motifs of Cel5H are identified herein by reference to amino acid positions, such reference is to the mature form of Cel5H, such as in particular that shown in SEQ ID NO: 3.

As used herein, the term "homology" denotes structural similarity between two macromolecules, particularly between two polypeptides or polynucleotides, from same or different taxons, wherein said similarity is due to shared ancestry. Hence, the term "homologues" denotes so-related macromolecules having said structural similarity. Preferably, homologues of the Cel5H polypeptide as intended herein encompass said homologues with native sequence.

A polypeptide homologue of the Cel5H polypeptide may preferably show at least about 30%, more preferably at least 40%, even more preferably at least 50%, still more preferably at least 60%, yet more preferably at least 70%, such as very preferably at least 80% or at least 90% or at least 95% sequence identity as defined elsewhere in this specification to the Cel5H polypeptide. Alternatively or preferably in addition, a polypeptide homologue of the Cel5H polypeptide may show at least about 50%, more preferably at least 60%, even more preferably at least 70%, still more preferably at least 80%, yet more preferably at least 90%, such as very preferably at least 95% sequence similarity as defined elsewhere in this specification to the Cel5H polypeptide. Further preferably, a polypeptide homologue of the Cel5H polypeptide may comprise one or more functional domains corresponding to the domains of the Cel5H polypeptide, and preferably one or more of GH family 5 catalytic domain, CBM family 6 domain and DZ domain. Preferably, said domains may have organisation analogous to Cel5H, in particular GH5-CBM6-DZ, usually with interposing linkers.

As noted, preferred homologues of the Cel5H polypeptide are the ACLA polypeptides of *Pseudomonas* sp. ND137. Exemplary ACLA polypeptides includes without limitation the sequence as annotated under the Uniprot/Swissprot accession number Q8VUT3 (sequence version 1 entered on Mar. 1, 2002) also reproduced in FIG. 1D (SEQ ID NO: 4). This sequence corresponds to ACLA precursor comprising the signal sequence. An exemplary mature ACLA polypeptide, i.e., with the signal sequence processed away, is represented by amino acid positions 28 to 585 of the respective precursor, as exemplarily reproduced in FIG. 1E (SEQ ID NO: 5).

One shall appreciate that the actual cleavage by signal peptidase may potentially occur at a peptide bond nearby the predicted cleavage site between amino acids 27 and 28 of the precursor ACLA such as shown in FIG. 1D (SEQ ID NO:4). For example, the actual cleavage might occur at any of the peptide bonds within the amino acid region from position 23 to 32, preferably 24 to 31, more preferably 25 to 30, even more preferably 26 to 29, of the precursor ACLA such as shown in FIG. 1D.

Depending on context readily understood by a skilled person, a reference herein to the ACLA polypeptide may encompass said mature form and/or said precursor forms. Further, unless indicated otherwise expressly or by context, whenever domains or other motifs of ACLA are identified herein by reference to amino acid positions, such reference is to the mature form of ACLA, such as in particular that shown in SEQ ID NO: 5.

The term "fragment" with reference to a given polypeptide such as Cel5H or a homologue thereof, or with reference to a given domain such as the DZ domain of the Cel5H or homologue thereof, generally refers to a truncated form of said polypeptide that has an N-terminal and/or C-terminal deletion of one or more amino acid residues as compared to said polypeptide such as said Cel5H or homologue or said domain, but where the remaining primary sequence of the fragment is identical to the corresponding positions in the amino acid sequence of said polypeptide such as said Cel5H or homologue or said domain.

For example, a fragment of a given polypeptide such as Cel5H or a homologue thereof, may include a sequence of about ≥5 consecutive amino acids, preferably ≥10 consecutive amino acids, more preferably ≥20 consecutive amino acids, even more preferably ≥30 consecutive amino acids, e.g., ≥40 consecutive amino acids, and most preferably ≥50 consecutive amino acids, e.g., ≥60, ≥70, ≥80, ≥90, ≥100, ≥200 or ≥500 consecutive amino acids of said polypeptide such as said Cel5H or homologue.

For example, a fragment of the DZ domain of Cel5H or a homologue thereof, may include a sequence of about ≥5 consecutive amino acids, preferably ≥10 consecutive amino acids, more preferably ≥20 consecutive amino acids, even more preferably ≥30 consecutive amino acids, e.g., ≥40 consecutive amino acids, and most preferably ≥50 consecutive amino acids, e.g., ≥60, ≥70, ≥80, or ≥90, consecutive amino acids of said DZ domain or homologue thereof.

Further, a fragment of a given polypeptide such as Cel5H or a homologue thereof or DZ domain may represent at least about 30%, e.g., at least 50% or at least 70%, preferably at least 80%, e.g., at least 85%, more preferably at least 90%, and yet more preferably at least 95% or even about 99% of the amino acid sequence of said polypeptide such as said Cel5H or homologue or DZ domain.

The term "variant" of a given polypeptide such as Cel5H or a homologue thereof or of a DZ domain refers to polypeptides the amino acid sequence of which is substantially identical (i.e., largely but not wholly identical) to a native sequence of said polypeptide such as said Cel5H or a homologue thereof or a DZ domain. "Substantially identical" refers to at least about 85% identical, e.g., preferably at least 90% identical, e.g., at least 91% identical, 92% identical, more preferably at least 93% identical, e.g., 94% identical, even more preferably at least 95% identical, e.g., at least 96% identical, yet more preferably at least 97% identical, e.g., at least 98% identical, and most preferably at least 99% identical.

Sequence identity between two polypeptides can be determined by optimally aligning (optimal alignment of two protein sequences is the alignment that maximises the sum of pair-scores less any penalty for introduced gaps; and may be preferably conducted by computerised implementations of algorithms, such as "Gap", using the algorithm of Needleman and Wunsch 1970 (J Mol Biol 48: 443-453), or "Bestfit", using the algorithm of Smith and Waterman 1981 (J Mol Biol 147: 195-197), as available in, e.g., the GCG™ v. 11.1.2 package from Accelrys) the amino acid sequences of the polypeptides and scoring, on one hand, the number of positions in the alignment at which the polypeptides contain the same amino acid residue and, on the other hand, the number of positions in the alignment at which the two polypeptides differ in their sequence. The two polypeptides differ in their sequence at a given position in the alignment when the polypeptides contain different amino acid residues at that position (amino acid substitution), or when one of the polypeptides contains an amino acid residue at that position while the other one does not or vice versa (amino acid insertion or deletion). Sequence identity is calculated as the proportion (percentage) of positions in the alignment at which the polypeptides contain the same amino acid residue versus the total number of positions in the alignment. Further suitable algorithms for performing sequence alignments and determination of sequence identity include those based on the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250), such as using defaults settings thereof.

The variant of a given polypeptide such as Cel5H or a homologue thereof or a DZ domain, as used herein, also specifically encompasses polypeptides having a certain degree of similarity to said polypeptide such as said Cel5H or a homologue thereof or a DZ domain. Preferably, such variants can be at least about 90% similar, e.g., preferably at least 91% similar, e.g., at least 92% similar, 93% similar, more preferably at least 94% similar, e.g., 95% similar, even more preferably at least 96% similar, e.g., at least 97% similar, yet more preferably at least 98% similar, e.g., at least 99% similar.

Sequence similarity between two polypeptides can be determined by optimally aligning (see above) the amino acid sequences of the polypeptides and scoring, on one hand, the number of positions in the alignment at which the polypeptides contain the same or similar (i.e., conservatively substituted) amino acid residue and, on the other hand, the number of positions in the alignment at which the two polypeptides otherwise differ in their sequence. The two polypeptides otherwise differ in their sequence at a given position in the alignment when the polypeptides contain non-conservative amino acid residues at that position, or when one of the polypeptides contains an amino acid residue at that position while the other one does not or vice versa (amino acid insertion or deletion). Sequence similarity is calculated as the proportion (percentage) of positions in the alignment at which the polypeptides contain the same or similar amino acid residue versus the total number of positions in the alignment.

It shall be understood that under reference to fragments and/or variants the specification also broadly contemplates fragments of variants of a given polypeptide such as Cel5H or a homologue thereof or a DZ domain, as well as variants of fragments of such polypeptide.

The term "functional" with reference to the fragments and/or variants of a given polypeptide such as Cel5H or a homologue thereof or a DZ domain denotes that such fragments and variants at least partly retain the biological activity or functionality of the corresponding polypeptide such as said Cel5H or homologue thereof or DZ domain. Preferably, such functional fragments and/or variants may retain at least about 20%, e.g., at least 30%, or at least 40%, or at least 50%, e.g., at least 60%, more preferably at least 70%, e.g., at least 80%, yet more preferably at least 85%, still more preferably at least 90%, and most preferably at least 95% or even 100% of the activity of the corresponding polypeptide such as said Cel5H or homologue thereof or DZ domain. Potentially, such functional fragments and/or variants may even have higher activity than the corresponding polypeptide such as said Cel5H or homologue or DZ domain.

Functional fragments and/or variants of a given polypeptide such as Cel5H or homologue thereof or DZ domain may be functionally equivalent to said polypeptide in at least one and preferably more or all aspects of its biological activity or function. Relevant aspects of biological function of said Cel5H or homologue thereof include in particular but without limitation cellulose-depolymerising or cellulase activity, activity profile with respect to different cellulose substrates (e.g., crystalline, semi-crystalline or amorphous cellulose or hemicellulose), ability or preference to degrade crystalline cellulose substrates, and ability to interact with or bind to cellulose substrates. Relevant aspects of biological function of said DZ domain of Cel5H or homologue thereof include in particular but without limitation cellulose-binding and particularly crystalline cellulose-binding, and/or oligomerisation activities. The biological activity of a given fragment and/or variant of Cel5H or of homologue thereof or of DZ domain, including the above aspects of such activity, can be determined by standard tests, such as for example the enzyme activity tests presented in the examples section.

The terms "solventogenic" or "solvent-producing" have their art-established meaning and in particular denote the ability of microorganisms such as bacteria (i.e., solventogenic bacteria) to produce one or more non-gaseous organic liquids or solvents, such as inter alia ethanol, acetone, butanol, propionic acid, butyric acid, ether or glycerine, from a carbohydrate source such as for example hexoses, pentoses or oligosaccharides. In particular, the term encompasses naturally occurring solventogenic organisms, solventogenic organisms with naturally occurring or induced mutations, and solventogenic organisms which have been genetically modified.

The terms "ethanologenic" or "ethanol-producing" is intended to denote the ability of microorganisms such as bacteria (i.e., ethanologenic bacteria) to produce at least or preferably mainly ethanol from a carbohydrate source such as for example hexose, pentose or oligosaccharides, more preferably to produce ethanol from carbohydrates as the most abundant non-gaseous fermentation product. In particular, the term encompasses naturally occurring ethanologenic organisms, ethanologenic organisms with naturally occurring or induced mutations, and ethanologenic organisms which have been genetically modified. Examples of suitable solventogenic microorganism include but are not limited to strains of *Clostridium* and *Zymomonas*, such as, but not limited to those exemplified herein.

The term "isolating" with reference to a particular component generally denotes separating that component from at least one other component of a composition from which the former component is thereby "isolated". In particular, the terms "isolating" and "isolated" may refer herein to increasing amount of a desired protein(s) or polypeptide(s) in a sample. The relative amount may be expressed as the ratio between the concentration or amount of the desired protein(s) or polypeptide(s) to be isolated and the concentration or amount of total proteins in the sample. In addition, the term may encompass separating desired protein(s) or polypeptide(s) from non-protein cellular components (e.g., cell walls, lipids, nucleic acids, etc.).

The terms "recombinant nucleic acid" or "recombinant nucleic acid molecule" as used herein generally refer to nucleic acid molecules (such as, e.g., DNA, cDNA or RNA molecules) comprising segments generated and/or joined together using recombinant DNA technology, such as for example molecular cloning and nucleic acid amplification. Usually, a recombinant nucleic acid molecule may comprise one or more non-naturally occurring sequences, and/or may comprise segments corresponding to naturally occurring sequences that are not positioned as they would be positioned in a source genome which has not been modified. When a recombinant nucleic acid molecule replicates in the host organism into which it has been introduced, the progeny nucleic acid molecule(s) are also encompassed within the term "recombinant nucleic acid molecule".

In particular embodiments, a recombinant nucleic acid molecule can be stably integrated into the genome of a host organism, such as for example integrated at one or more random positions or integrated in a targeted manner, such as, e.g., by means of homologous recombination, or the recombinant nucleic acid molecule can be present as or comprised within an extra-chromosomal element, wherein the latter may be auto-replicating.

Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates); Innis et al., PCR Protocols: A Guide to Methods and Applications, Academic Press: San Diego, 1990. General principles of microbiology are set forth, for example, in Davis, B. D. et al., Microbiology, 3d edition, Harper & Row, publishers, Philadelphia, Pa. (1980).

The term "recombinant polypeptide" as used herein refers to a polypeptide or protein produced by a host organism through the expression of a recombinant nucleic acid molecule, which has been introduced into said host organism or an ancestor thereof, and which comprises a sequence encoding said polypeptide or protein.

Further, the terms "recombinant" or "transformed" as used herein with reference to host organisms, microorganisms or cells, encompass such host organisms, microorganisms or cells into which a recombinant nucleic acid molecule has been introduced, as well as the recombinant progeny of such host organisms, microorganism or cells.

Hence, the term "transformation" encompasses the introduction or transfer of a foreign nucleic acid such as a recombinant nucleic acid into a host organism, microorganism or cell. The so-introduced nucleic acid may be preferably maintained throughout the further growth and cell division of said host organism, microorganism or cell. Any conventional gene transfer methods may be used to achieve transformation, such as without limitation electroporation, electropermeation, chemical transformation, lipofection, virus- or bacteriophage-mediated transfection, etc.

By "encoding" is meant that a nucleic acid sequence or part(s) thereof corresponds, by virtue of the genetic code of an organism in question to a particular amino acid sequence, e.g., the amino acid sequence of a desired polypeptide or protein. By means of example, nucleic acids "encoding" a particular polypeptide or protein may encompass genomic, hnRNA, pre-mRNA, mRNA, cDNA, recombinant or synthetic nucleic acids.

Preferably, a nucleic acid encoding a particular polypeptide or protein may comprise an open reading frame (ORF) encoding said polypeptide or protein. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a polypeptide. Hence, the term may be synonymous with "coding sequence" as used in the art.

In an embodiment, the nucleic acid sequence or ORF encoding the present polypeptide(s) may be codon optimised as known per se for expression in a particular organism, e.g., microorganism, more particularly a bacterium of interest. Codon usage bias and codon frequencies from various organisms are available, for example via the Codon Usage Database (www.kazusa.or.jp/codon/) described by Nakamura et al. 2000 (Nucl Acids Res 28:292).

Expression of polypeptides of interest in recombinant microorganisms as taught herein can be achieved through operably linking the nucleic acid sequences or ORF(s) which encode said polypeptides with regulatory sequences allowing for expression in said microorganisms. In this regard, the term "expressing" a polypeptide when referring to a recombinant organism encompasses recombinant organisms capable of expressing the polypeptide, e.g. under suitable culture conditions or upon addition of inducers (e.g. where inducible regulatory sequences are used).

An "operable linkage" is a linkage in which regulatory nucleic acid sequences and sequences sought to be expressed are connected in such a way as to permit said expression. For example, sequences, such as, e.g., a promoter and an ORF, may be said to be operably linked if the nature of the linkage between said sequences does not: (1) result in the introduction of a frame-shift mutation, (2) interfere with the ability of the promoter to direct the transcription of the ORF, (3) interfere with the ability of the ORF to be transcribed from the promoter sequence.

The precise nature of regulatory sequences or elements required for expression may vary between organisms, but typically include a promoter and a transcription terminator, and optionally an enhancer.

Reference to a "promoter" or "enhancer" is to be taken in its broadest context and includes transcriptional regulatory sequences required for accurate transcription initiation and where applicable accurate spatial and/or temporal control of gene expression or its response to, e.g., internal or external (e.g., exogenous) stimuli. More particularly, "promoter" may depict a region on a nucleic acid molecule, preferably DNA molecule, to which an RNA polymerase binds and initiates transcription. A promoter is preferably, but not necessarily, positioned upstream, i.e., 5', of the sequence the transcription of which it controls. Typically, in prokaryotes a promoter region may contain both the promoter per se and sequences which, when transcribed into RNA, will signal the initiation of protein synthesis (e.g., Shine-Dalgarno sequence).

In embodiments, promoters contemplated herein may be constitutive or inducible.

By means of example, constitutive promoters suitable for expression in *Clostridium* species such as *Clostridium acetobutylicum* include without limitation the promoter of the thiolase gene of *C. acetobutylicum* (P$_{thl}$ promoter), the promoter of the acetoacetate decarboxylase gene (P$_{adc}$ promoter), the promoter of the phosphotransbutyrylase gene (P$_{ptb}$ promoter), the xylose-inducible promoter of the *Staphylococcus xylosus* xylose operon (P$_{xyl}$ promoter)

Hence, in particular embodiments a promoter is provided which is a promoter controlled by an operator. As used herein, the term "operator" refers to a nucleotide sequence, preferably DNA sequence, which controls the initiation and/or maintenance of transcription of a sequence from a promoter. Typically, an operator may be generally placed between a promoter and a downstream sequence the transcription of which the promoters controls. Usually, an operator is capable of binding a repressor polypeptide, whereby it reduces the transcription from the said promoter. A useful repressor can alternate between a state in which it binds the operator and a state in which it does not and such alternation may be advantageously controlled by an external condition, e.g., an external substance or a particular metabolite. Accordingly, in host cells comprising a compatible repressor, the inclusion of an operator in the nucleic acid of the invention may allow to control the activity of the promoter and expression there from. Operator sequences may be generally derived from bacterial chromosomes.

It shall also be appreciated that the nucleic acids of the invention may encode one or more than one polypeptides of interest. Moreover, where expression of two or more polypeptides is intended, said expression may be from independent expression units, or may be from a single expression unit (i.e., multi-cistronic expression) comprising two or more sequential ORFs controlled by common regulatory elements. By means of example, an expression unit encoding two or more polypeptides may be generated by associating translation initiation codons of the respective ORFs with sequences controlling translation initiation (e.g., ribosome entry sequences).

The terms "terminator" or "transcription terminator" refer generally to a sequence element at the end of a transcriptional unit which signals termination of transcription. For example, a terminator is usually positioned downstream of, i.e., 3' of ORF(s) encoding a polypeptide of interest. For instance, where a recombinant nucleic acid contains two or more ORFs, e.g., successively ordered and forming together a multi-cistronic transcription unit, a transcription terminator may be advantageously positioned 3' to the most downstream ORF.

In a preferred embodiment, regulatory sequences controlling the expression of polypeptide(s) as taught herein may be advantageously provided on the recombinant nucleic acid to be used for transforming the present microorganisms. However, also contemplated are embodiments in which the recombinant nucleic acid provides for coding sequence(s) lacking one or more regulatory sequences, whereas the required regulatory sequences are provided by the transformed microorganism (such as, e.g., wherein the recombinant nucleic acid inserts into a chromosomal or episomal region comprising suitable regulatory sequences).

*Clostridium* and *Clostridium acetobutylicum* as used herein refer to bacterial taxons known as such in the art, and particularly encompass bacteria, bacterial species, strains, subspecies and cultures belonging to said taxons, as well as modified or engineered, such as for example mutated or genetically engineered, derivatives of naturally-occurring or wild-type specimens. By means of guidance and not limitation, isolated strains of *Clostridium* available from the American Type Culture Collection (ATCC) can be ordered inter alia under accession numbers ATCC 824, ATCC 4259, ATCC 39236 or ATCC 43084 for *Clostridium acetobutylicum*. Isolated strains of *Clostridium beijerinckii* can, for example be ordered inter alia under accession numbers ATCC 858 and ATCC 25752.

As noted, the polypeptides expressed by the present solventogenic microorganisms may be targeted for secretion. To achieve secretion, a nucleic acid sequence encoding a polypeptide may be operably linked to a sequence encoding a secretion signal sequence. In this connection, "operably linked" denotes that the sequence encoding the signal sequence and the sequence encoding the polypeptide to be secreted are connected in frame or in phase, such that upon expression the signal peptide facilitates the secretion of the polypeptide so-linked thereto.

It shall be appreciated that suitable signal sequences may depend on the type of microorganism in which secretion is desired. For example, distinct signal sequences may be required in Gram-positive bacteria vs. Gram-negative bacteria.

By means of example and not limitation, secretion in Gram-positive bacteria, and in particular in *Clostridium* such as *C. acetobutylicum*, may be achieved using the signal sequence of the Cel5A precursor polypeptide of *C. cellulolyticum* (exemplary sequence: Genbank acc. no. AAA51444, seq version 1 revised on Oct. 31, 1994), or of the CipC precursor scaffolding protein of *C. cellulolyticum* (exemplary sequence: Genbank acc. no. AAC28899, seq. version 2 revised on Dec. 5, 2005), or of the CipA precursor scaffolding protein of *C. acetobutylicum* (exemplary sequence: Genbank acc. no. AAK78886, seq. version 1 revised on Jan. 19, 2006).

Further without limitation, secretion in Gram-negative bacteria, may be achieved via the Sec pathway, e.g., using the signal sequence of the gluconolactonase precursor polypeptide of *Z. mobilis* (exemplary sequence: Genbank acc. no. CAA47637, seq. version 1 revised on Oct. 19, 2006) or of the carbohydrate selective porine OprB (exemplary sequence: Genbank acc. no. AAV88688, seq. version 1 revised on Jan. 25, 2005), or via the twin-arginine translocation (Tat) pathway, e.g., using the signal sequence of the gluco fructose oxidoreductase precursor polypeptide of *Z. mobilis* (exemplary sequence: Genbank acc. no. CAB02496, seq. version 1 revised on Oct. 19, 2006).

It shall also be appreciated that native (or homologous, endogenous) signal peptides of polypeptides to be expressed by the microorganisms as taught herein may be employed, insofar they are functional in said microorganisms. Hence, by means of example, secretion of Cel5H or related polypeptides may be achieved using the endogenous or homologous secretion signal sequence of the Cel5H precursor polypeptide. In particular, since *S. degradans* is a Gram-negative bacterium, the endogenous or homologous signal sequence of Cel5H may be particularly suited for secretion thereof in other Gram-negative bacteria. In other embodiments, polypeptides such as Cel5H and related polypeptides may be secreted using heterologous signal sequences.

Figure 9:
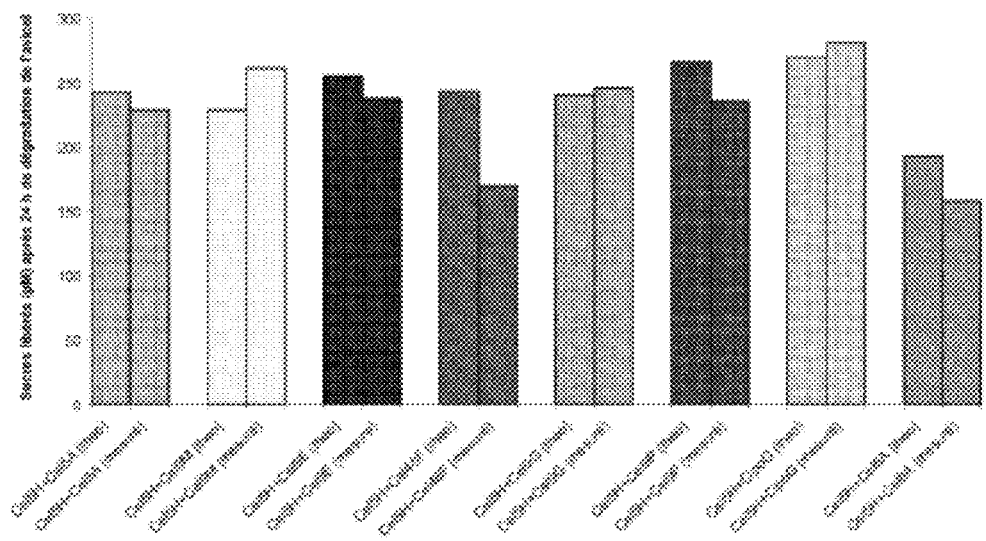
FIG. 9 shows the degradation of Avicel by Cel5H and at least one other cellulase enzyme according to particular embodiments of the invention.

The domain structure of the native Cel5H polypeptide can be outlined as GH5-PSL-CBM6-EPR-DZ, with schematic indication of the domain boundaries in mature Cel5H shown in FIG. 9. Functional fragments of Cel5H or homologues thereof preferably contain one or more of the GH5, CBM6 and DZ domains, or domains corresponding thereto (e.g., analogous domains within a homologue and/or variant of Cel5H). Preferably, domains comprised in such fragments may be functional as intended herein. Hence, in particular embodiments the invention contemplates fragments such as those corresponding to of the following domain organisations: GH5, GH5-PSL, GH5-PSL-CBM6, GH5-PSL-CBM6-EPR, PSL-CBM6, PSL-CBM6-EPR, PSL-CBM6-EPR-DZ, CBM6, CBM6-EPR, CBM6-EPR-DZ, and EPR-DZ, DZ. The invention further envisages fragments corresponding to combinations of the domains of mature Cel5H, such as, but not limited to EPR-DZ-EPR-DZ.

As noted, the invention also relates to various fusions of Cel5H and related polypeptides with useful heterologous domains. In this context, the term "heterologous" denotes that said domain(s) are derived from polypeptides other than the Cel5H polypeptide or the homologue thereof. Accordingly, "heterologous" when referring to combinations of domains refers to the fact that the different domains do not originate from (or do not naturally occur in) the same protein. Nevertheless, fusions of additional Cel5H-derived domain(s) with Cel5H polypeptide or homologue thereof, or fragments and/or variants thereof, can also be contemplated.

The term "fusion" is broadly contemplated herein as encompassing inter alia genetic fusions (i.e., fusing distinct parts into a single open reading frame) as well as fusions induced by chemical and/or physical means (e.g., chemical cross-linking or photo-coupling). Furthermore, fusion includes direct fusion or fusion via a linker. Suitable linkers may include without limitation peptide sequences of at least 3, preferably at least 4 or 5, more preferably at least 7, and yet more preferably at least 12 amino acids, such as between 3 and 15 amino acids, and preferably comprising, being enriched for or consisting of non-charged amino acids, preferably chosen from glycine, serine, cysteine, asparagine, tyrosine, glutamine, alanine, valine, proline, threonine, and more preferably glycine or serine.

Exemplary glycoside hydrolase (GH) catalytic domains may be derived from glycoside hydrolases (glycosidases) known per se or future ones identified and isolated inter alia using established procedures. Exemplary glycosidases include those grouped under the EC 3.2.1. "Glycosidases" classification of NC-IUBMB, more preferably glycosidases capable of depolymerising cellulosic and lingo-cellulosic substrates, such as, e.g., cellulases (EC 3.2.1.4.), cellulose 1,4-β-cellobiosidases (EC 3.2.1.91) and processive endocellulases (EC 3.2.1.4./EC 3.2.1.91.).

The term carbohydrate-binding module(s) (CBM) is known in the art and commonly broadly covers all non-catalytic sugar- or carbohydrate-binding modules found in or derived from glycoside hydrolases. CBM modules preferred herein may include those binding specifically to cellulose or cellulosic substrates and alternatively referred to as cellulose-binding domains (CBD). CMB and their structural and functional properties are reviewed inter alia in Tomme et al. 1995 ("Cellulose-binding domains: classification and properties", in Enzymatic Degradation of Insoluble Polysaccharides, Saddler J N & Penner M, eds., pp. 142-163, American Chemical Society, Washington) and Boraston et al. 2004 ("Carbohydrate-binding modules: fine tuning polysaccharide recognition". Biochem J 382: 769-81).

Cohesin-binding domains as used herein refer generally to all polypeptide domains capable of specifically binding to one or more receptor (cohesin) domains of cellulosomal scaffoldin subunits. Exemplary cohesin-binding domains include dockerin domains found in or derived from glycoside hydrolases that assemble to cellulosomes. Both type I and type II dockerin domains are contemplated herein. Dockerin domains are explained inter alia in Lytle et al. 2001 ("Solution structure of a type I dockerin domain, a novel prokaryotic, extracellular calcium-binding domain". J Mol Biol 307: 745-753), Adams et al. 2005 ("Structural characterization of type II dockerin module from the cellulosome of *Clostridium thermocellum*: calcium-induced effects on conformation and target recognition". Biochemistry 44: 2173-82) and in Bayer et al. 1998 ("Cellulosomes-structure and ultrastructure". J Struct Biol 124: 221-234). A suitable assay for determining dockerin-cohesin interactions, such as to guide the choice of a suitable dockerin domain herein, is described inter alia in Haimovitz et al. 2008 ("Cohesin-dockerin microarray: Diverse specificities between two complementary families of interacting protein modules". Proteomics 8: 968-979).

Further contemplated is co-expression and optionally co-secretion of polypeptides taught herein with other polypeptides or enzymes, preferably recombinant polypeptides or enzymes, useful in carbohydrate polymer metabolism, particularly in cellulose metabolism. The term "co-expression" generally relates to expression of two or more proteins or polypeptides (said to be "co-expressed") by the same microorganism, particularly by a same cell of said microorganism. Suitable systems for achieving co-expression of two or more polypeptides are known per se. Without limitation, co-expressed polypeptides may be encoded by separate cistrons controlled by the same or different regulatory elements, or may be encoded by a single multi-cistronic element; such cistrons may be on a chromosome or on same or different epigenetic elements, or combinations thereof etc.

The terms "glycoside hydrolase" or "glycosidase" generally encompass enzymes and enzyme complexes capable of hydrolysing glycosidic linkages, more particularly O-, N- or S-glycosidic linkages, even more preferably such linkages in oligosaccharide and/or polysaccharide substrates. The terms encompass exoglycosidases as well as endoglycosidases. The terms particularly encompass glycosidases grouped under the EC 3.2.1. "Glycosidases" classification of NC-IUBMB.

The term "cellulase" generally encompasses enzymes and enzyme complexes capable of hydrolysing cellulose and cellulose-containing substrates. The term encompasses without limitation the following cellulase types: cellobiohydrolase(1, 4-β-D-glucan cellobiohydrolase, EC 3.2.1.91), endo-β-1,4-glucanase (endo-1,4-β-D-glucan 4-glucanohydrolase, EC 3.2.1.4), processive endocellulase (EC 3.2.1.4./EC 3.2.1.91.) and β-glucosidase (EC 3.2.1.21). Cellulases further encompass endoglucanases as well as (processive) exoglucanases, and cover enzymes which produce monomers and/or oligomers of various lengths. The term may also encompass cellobiases, oxidative cellulases, glucosidases, cellulose phosphorylases, and other enzymes commonly denoted thereby. The term encompasses enzymes capable of degrading various forms of cellulose, such as without limitation crystalline cellulose, semi-crystalline cellulose, amorphous cellulose, hemicellulose and/or chemically or biologically modified cellulose forms.

By means of example and not limitation, the cellulolytic system of *Clostridium cellulolyticum* has been reviewed by Belaich et al. 1997 ("The cellulolytic system of *Clostridium cellulolyticum*". J Biotechnol 57: 3-14); and of *Saccharophagus degradans* in Taylor et al. 2006 (supra).

The invention further contemplates engineered cellulosomes comprising polypeptides, particularly Cel5H and related polypeptides (e.g., DZ-domain and polypeptides comprising such), as taught herein. As known in the art, native cellulosomes represent extracellular, multienzyme cellulolytic complexes of certain bacterial taxons, such as inter alia *Clostridium* and *Bacteroides*. The basic organisation of native cellulosomes involves an organising polypeptide (scaffoldin), commonly comprising one or more same or distinct carbohydrate-binding modules (CBM) and one or more same or distinct receptor (cohesin) domains that facilitate integration of glycosidases or cellulolytic enzymes into the cellulosome complex through interaction with cognate dockerin domains in said enzymes.

These structural features of native cellulosomes may also be employed in engineered cellulosomes, whereby desired carbohydrate-binding and carbohydrate-depolymerising activities may be integrated into engineered cellulosomes. Techniques for producing engineered cellulosomes are established in the art (see, e.g., Fierobe et al. 2002 ("Degradation of cellulose substrates by cellulosome chimeras. Substrate targeting versus proximity of enzyme components". J Biol Chem 277: 49621-30); Fierobe et al. 2005 ("Action of designer cellulosomes on homogeneous versus complex substrates: controlled incorporation of three distinct enzymes into a defined trifunctional scaffoldin". J Biol Chem 280: 16325-34); and Perret et al. 2004 ("Production of heterologous and chimeric scaffoldins by *Clostridium acetobutylicum* ATCC 824". J Bacteriol 186: 253-7)).

Commonly, an engineered cellulosome may contain a hybrid or chimeric scaffoldin polypeptide comprising one or more CBM modules of the same or divergent carbohydrate substrate specificity, and one or more cohesin domains capable of binding the same or divergent cognate dockerin domains. Enzymes, such as particularly glycosidases or cellulolytic enzymes, may be incorporated into the cellulosome by means of cognate dockerin modules (normally present in and/or engineered into said enzymes) for the cohesin domains found in the scaffoldin polypeptide. Said enzymes may also comprise CBM or other non-catalytic domains. Such engineered cellulosomes are commonly known in the art as "chimeric" or "hybrid" cellulosomes or "minicellulosomes".

Alternatively or additionally, the one or more enzymes, such as glycosidases or cellulolytic enzymes, may be covalently linked with the scaffoldin backbone, such as, e.g., by being expressed as a part of the same polypeptide chain (i.e., genetic fusion). Such cellulosomes are commonly known as "covalent" (Mingardon et al. 2007, "Exploration of new geometries in cellulosome-like chimeras" Appl. Environ. Microbiol. 73: 7138-7149).

Hence, engineered cellulosomes, such as hybrid, chimeric, mini-, or covalent cellulosomes, or any combination of these modalities, or any other engineered cellulosome forms, are contemplated for use with the polypeptides taught herein.

The term "cellulose" is known per se in the art. By means of further explanation and not limitation, the term may encompass all forms of cellulose, such as without limitation naturally and non-naturally occurring cellulose forms, such as, e.g., crystalline cellulose, semi-crystalline cellulose, microcrystalline cellulose, amorphous cellulose, hemicellulose, regenerated cellulose, and/or chemically or biologically modified or derivatised cellulose forms, such as, e.g., ethers or esters thereof, etc.

A substance enriched in crystalline cellulose may comprise, without limitation, at least about 1% (w/w), e.g., ≥5% (w/w), preferably at least about 10% (w/w), e.g., ≥20%, ≥30% or ≥40% (w/w), more preferably at least about 50% (w/w), e.g., ≥60% or ≥70% (w/w), yet more preferably at least about 80% (w/w), e.g., ≥90% (w/w) of crystalline cellulose, semi-crystalline and/or microcrystalline cellulose as understood in the art, more preferably of crystalline cellulose.

Methods and processes for treating or contacting cellulose-containing substances with recombinant microorganisms such as taught herein are generally known in the art, and may without limitation comprise industrial fermentation processes of various scale. The material to be so-fermented may be provided, e.g., in solid, semi-solid, liquid or soluble form, or as a homogenate or extract, or as a (aqueous) dispersion or suspension, or as (partly) isolated or purified and/or pre-treated (e.g., by dilute-acid pre-treatment, sodium hydroxide pretreatment, lime pre-treatment, pre-treatment with organic solvents with water, hydrothermal processes, or AFEX) lignocellulosic substrates or cellulosic substrates or cellulose, or in other suitable forms used per se for depolymerisation and/or fermentation of cellulosic materials and biomass. Accordingly, the invention also contemplates starter cultures comprising the microorganisms of the invention, optionally in combination with one or more other desired microorganisms. Biotechnological approaches for cellulose utilisation are reviewed inter alia in Lynd et al. 2002 ("Microbial cellulose utilization: fundamentals and biotechnology". Microbiol Mol Biol Rev 66: 506-77), and in Himmel et al. 2007 ("Biomass recalcitrance: engineering plants and enzymes for biofuels production" Science 315: 804-807).

The above aspects and embodiments are further supported by the following non-limiting examples.

EXAMPLES

Example 1

Identification of the Novel DZ Domain of Cel5H

The published analysis of the putative cellulases produced by *S. degradans* (Taylor et al. 2006, supra) indicated the following organisation for Cel5H (from N-terminal to C-terminal ends of the enzyme): signal sequence/catalytic module (GH-family 5)/serine-rich linker/carbohydrate binding module belonging to CBM-family 6/glutamic acid- and proline-rich-linker, in other denotation signal sequence-GH5-PSL-CBM6-EPR.

We have performed a more thorough sequence analysis which revealed the existence of a novel about 100-aminoacid long domain termed DZ domain at the C-terminus of Cel5H, from position 496 to position 596 in SEQ ID NO: 2 (FIG. 1B). Hence, the organisation of Cel5H can be denoted as signal sequence-GH5-PSL-CBM6-EPR-DZ. Since the DZ domain is rich in aromatic residues (Trp, Tyr) it may plausibly represent a new type of carbohydrate-binding module (CBM).

A search for homologous domains in non-redundant DNA sequence database revealed a highly homologous domain in the putative cellulase encoded by the ac/A gene from the bacterium *Pseudomonas* sp. ND137 (positions 465 to 558 of SEQ ID NO: 4, FIG. 1D). Other proteins containing this particular domain originate from *S. degradans*.

Another atypical feature of Cel5H is related to the GH5 catalytic module of which the length is estimated to 300 amino acids whereas other family-5 enzymes display catalytic modules of 380-450 residues. This module is therefore unusually short and lacks an important stretch of highly conserved residues among family-5 enzymes.

Example 2

Production of Entire (Wild-Type), Truncated Cel5H, and Engineered Forms of Cel5H in *E. coli*

Using molecular biology techniques the DNA encoding the mature form of Cel5H (without signal sequence) was amplified and cloned in an *E. coli* expression vector (pET22b (+), Novagen). The resulting vector was used to transform the *E. coli* strain BL21 (DE3) (Novagen). Similarly, modified genes encoding truncated or engineered forms of Cel5H were obtained by PCR and cloned in pET22b(+), prior to transformation of *E. coli* strain BL21 (DE3). In all cases, six His codons were grafted at the C-terminus extremity of the recombinant proteins to facilitate their purification on Nickel resin (Ni-NTA, Qiagen). The various engineered forms of Cel5H are summarised in FIG. 2.

The recombinant strains were grown in Luria Bertani medium and the expression of the cloned genes was triggered using IPTG as the inducer. The synthesis of the recombinant Cel5H was verified by denaturing polyacrylamide gel electrophoresis (SDS-PAGE). The cultures were centrifuged and the harvested cells were broken in a French press.

Example 3

Purification and Characterisation of the Various Forms of Cel5H and Evaluation of Activity on Various Substrates Including Carboxymethyl Cellulose (CMC), Phosphoric Acid-Swollen Cellulose (PASC), Avicel and a Raw Substrate, the Hatched Straw Cel5H, Cel5Ht and Cel5Ht-CBM3a were purified by loading the crude extract on Ni-NTA (Qiagen), and elution of the protein of interest using increasing concentrations of imidazolium. Purification was achieved using FPLC Q-sepharose (Hitrap Q HP resin, GE Healthcare) as described below.

Alternatively Cel5H but also Cel5H-CBM3a and CBM3a-Cel5H constructs were purified using a different procedure. The crude extract containing these proteins was incubated with PASO at 4° C., and centrifuged. The cellulose pellet was washed several times by centrifugation in phosphate buffer, and the proteins specifically bound to the cellulase were eluted from the matrix using pure water or 1% triethylamine. The purification was achieved by loading the fraction containing the protein of interest onto an anion exchanger resin (Hitrap Q HP, GE healthcare) at pH 8 using an FPLC device. The protein was eluted from the column using a linear gradient of NaCl. In all cases, purity was checked by SDS-PAGE, and the protein concentrated, divided into aliquots and stored at −80° C.

Activity of the purified enzymes was tested on CMC, PASC, Avicel, and hatched straw using standard conditions (37° C.).

Figure 3:
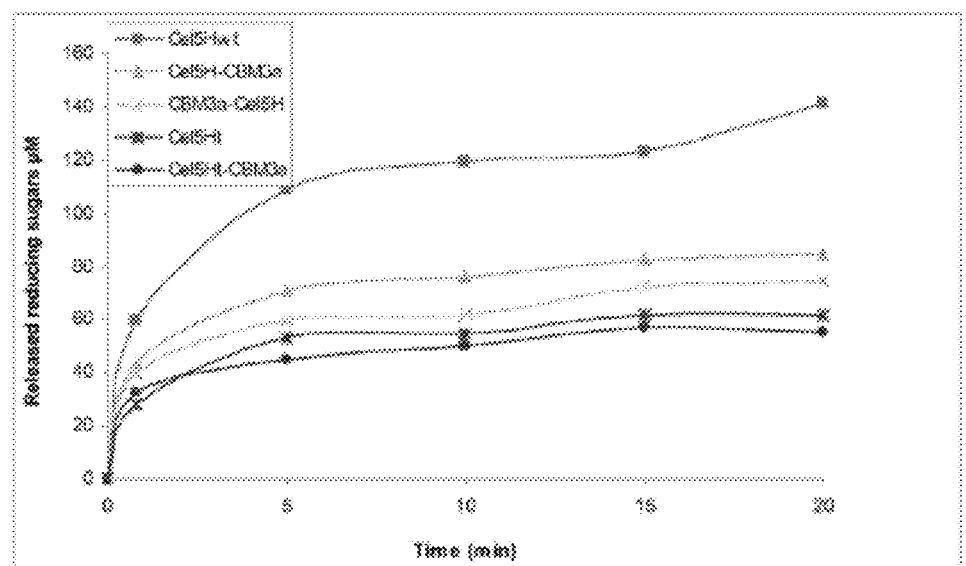
FIG. 3 illustrates activity of the various forms of Cel5H against CMC at 37°, according to particular embodiments of the invention.

For testing of activity on CMC, the enzyme concentration was 1 nM and substrate was at 8 g/L CMC (pH 6.0). Activity of the various forms of Cel5H against CMC at 37° is shown in FIG. 3. The activity pattern obtained in all cases suggests an exo mode of action for Cel5H rather than endo mode of action. As shown in FIG. 3, all enzymes are characterised by an important release of sugars within the first minutes or seconds of the kinetics, then the enzymatic activity is considerably reduced (observed plateau after 5 minutes), which is more typical of an exo-acting or processive enzyme.

Based on initial velocity, the specific activity of Cel5H was estimated at 20,000 iu/μmol on CMC.

Figure 4:
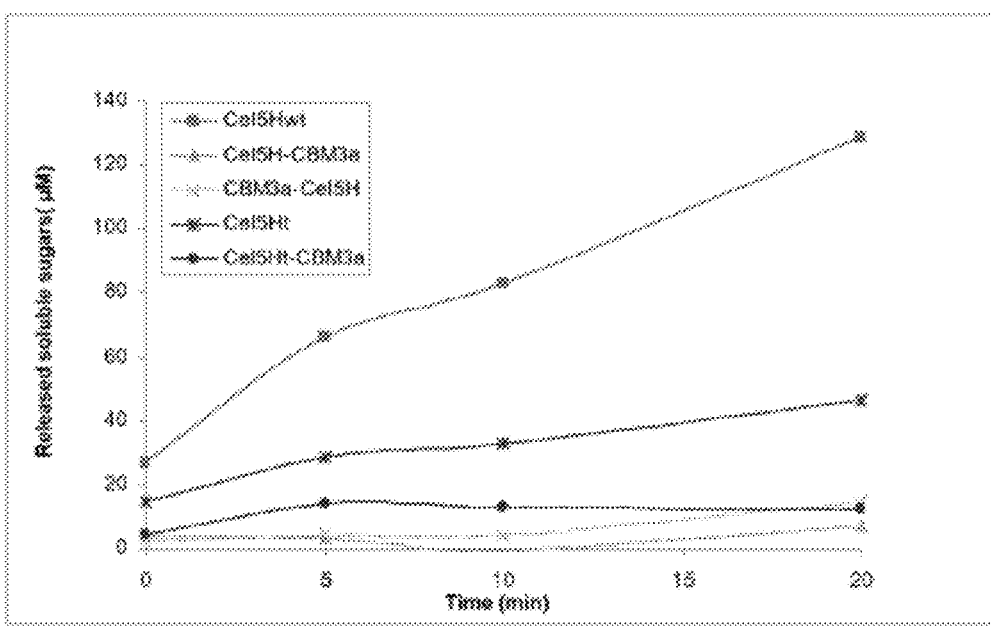
FIG. 4 illustrates activity of the various forms of Cel5H against Phosphoric Acid Swollen Cellulose at 37°, according to particular embodiments of the invention.

For testing of activity on PASO, the enzyme concentration was 5 nM and substrate was at 3.5 g/L (pH 6.0). Activity of the various forms of Cel5H against PASO at 37° is shown in FIG. 4.

Removal of the DZ domain (Cel5Ht) reduced the specific activity by approx. 70%, showing that this domain plays an important role during the hydrolysis of PASO by Cel5H. Based on these kinetics, the specific activity of Cel5Hwt on PASO is approx. 1,000 iu/μmol. Grafting a CBM3a at the N-terminus (CBM3a-Cel5H), the C-terminus (Cel5H-CBM3a) or instead of the DZ module (Cel5Ht-CBM3a) further reduced the activity of the enzyme.

Figure 5:
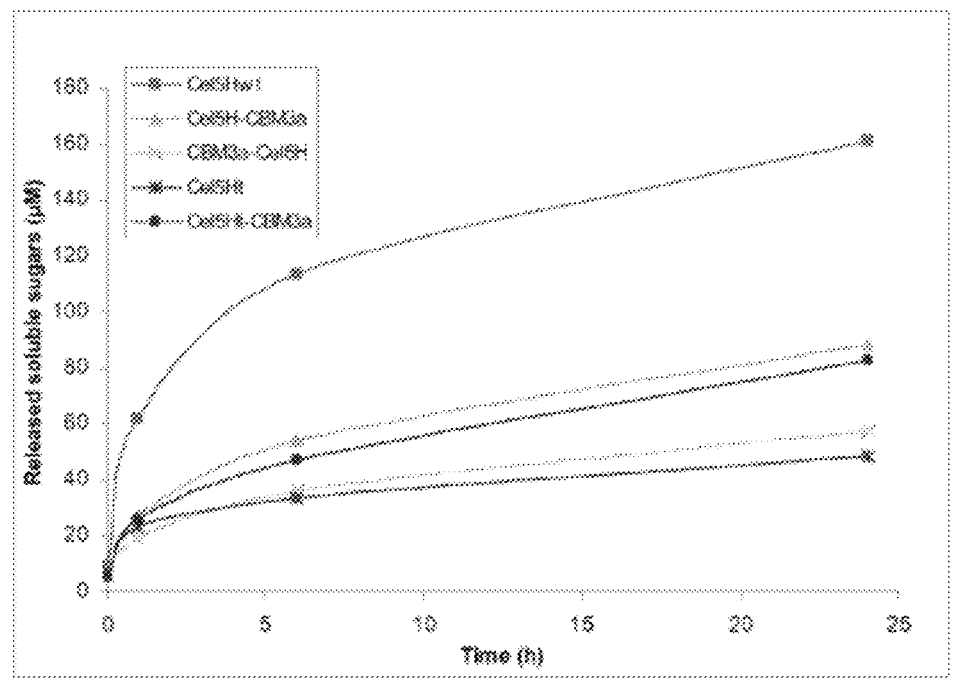
FIG. 5 illustrates activity of the various forms of Cel5H against Avicel PH101 at 37°, according to particular embodiments of the invention.

For testing of activity on Avicel, the enzyme concentration was 100 nM and substrate was at 3.5 g/L (pH 6.0). Activity of the various forms of Cel5H against Avicel at 37° is shown in FIG. 5.

As observed for the two other substrates, the activity of wild type Cel5H is higher than the engineered forms, and especially compared to the truncated form that lacks the C-terminal DZ domain, further confirming the role of the DZ domain in degradation of crystalline cellulose. Its replacement by the powerful CBM3a only partly restores the avicelase activity compared to wild type Cel5H. The activity of Cel5H on Avicel is elevated, being calculated on data obtained during the first hour of the kinetic reveals as a specific activity of 8.5±2 iu/μmol.

The enzymatic activity of Cel5H was also tested on the soluble chromogenic substrate, para-nitrophenyl-β-D-cellobioside. Upon cleavage by the enzyme of the link between the para-nitrophenyl group and the cellobiose, para-nitrophenol and cellobiose is liberated and its concentration can be directly determined by means of spectrophotometric analysis. The specific activity was about 14 ui/μmol for Cel5H on this substrate. This activity is about 13 times higher than the activity of Cel5A from *C. cellulolyticum*, which also belongs to the family 5 of glycoside hydrolases.

Example 4

Comparison of Cel5H Avicelase Activity with Wild Type and Engineered Cellulases from *C. cellulolyticum*

Using an assay design as described in example 3, the Cel5H avicelase activity was compared with wild type and engineered cellulases from *C. cellulolyticum*.

The enzyme concentration was 100 nM and substrate was at 3.5 g/L (pH 6.0).

Figure 6:
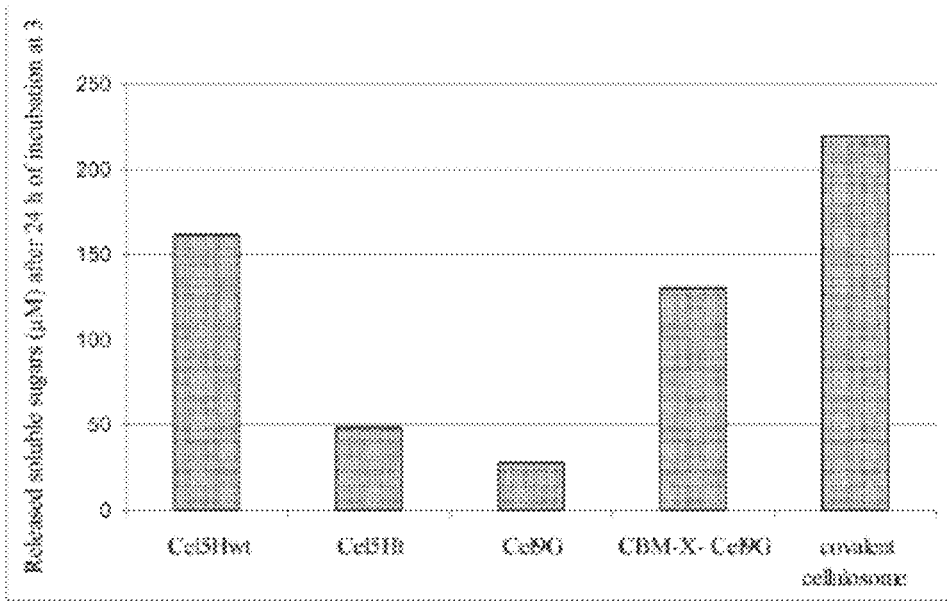
FIG. 6 illustrates comparison of Cel5H avicelase activity with wild type and engineered cellulases from *C. cellulolyticum*, according to particular embodiments of the invention.

As shown in FIG. 6, Cel5Hwt is almost 6-fold more active than Cel9G, one of the most active cellulases from *C. cellulolyticum* on Avicel. Compared to the engineered form of Cel9G which contains a CBM3a and an X2 module (CBM-X-Cel9G, Mingardon et al. 2007. Appl Environ Microbiol 73: 7138-49.), Cel5Hwt still remains 25% more active on crystalline cellulose. On the contrary, the covalent cellulosome (which includes the catalytic modules of Cel9G and Cel48F and the powerful CBM3a; Mingardon et al. 2007, supra) is merely 36% more active than Cel5H.

Analysis by dionex of the soluble sugars released by Cel5Hwt on Avicel indicates that after 24 hours of incubation the latter enzyme mainly releases cellobiose (67%), cellotriose (26.5%) and glucose (6.5%), i.e., soluble sugars of relatively low complexity, but no cellotetraose.

The activity of Cel5H (Cel5Hwt) was also tested on hatched straw (enzyme and substrate at 100 nM and 3.5 g/L, respectively). After 24 hours of incubation, approx. 70 μM of soluble sugars were released by Cel5Hwt. Analysis of the soluble sugars by dionex indicated that glucose (90%) was mainly released by Cel5H on this raw substrate.

All kinetic experiments described above were performed at 37° C. in 20 mM Tris-maleate pH 6.0, 1 mM $CaCl_2$ (azide 0.01% w/v) buffer. The avicelase activity of Cel5H was also measured in presence of 1% sodium chloride (171 mM NaCl) in the same buffer. In the presence of NaCl, Cel5H was found to be 10% more active.

The activity of the enzyme is considerably reduced at 50° C. compared to 37° C., possibly due to unfolding of the enzyme at 50° C.

In conclusion, Cel5H displays an elevated activity on crystalline cellulose and is therefore a suitable candidate for heterologous production in solvent producing bacteria such as *C. acetobutylicum*, to enable the growth of this strain on crystalline cellulose or amorphous cellulose. Our results suggest the DZ module acts as a cellulose binding module (CBM), which may advantageously anchor the cellulase at the surface of the substrate. Our data obtained so far indicate that this enzyme is likely to be an exoglucanase or an endoprocessive cellulase (and not an endoglucanase). It is worth noticing that family-5 cellulases are usually described as endoglucanases. Cel5H does not release any cellotetraose from pure cellulose, but produces cellobiose, glucose and cellotriose.

Example 5

4-Grafting Accessory Domains and/or Linkers of Cel5H to Other Enzyme(s)

The DZ module of *S. degradans* alone or with the upstream CBM6 and optionally a linker (see Cel5Hwt in FIG. 1) was adjoined to other enzyme(s) that lack such modules, using molecular genetic techniques.

Figure 7:
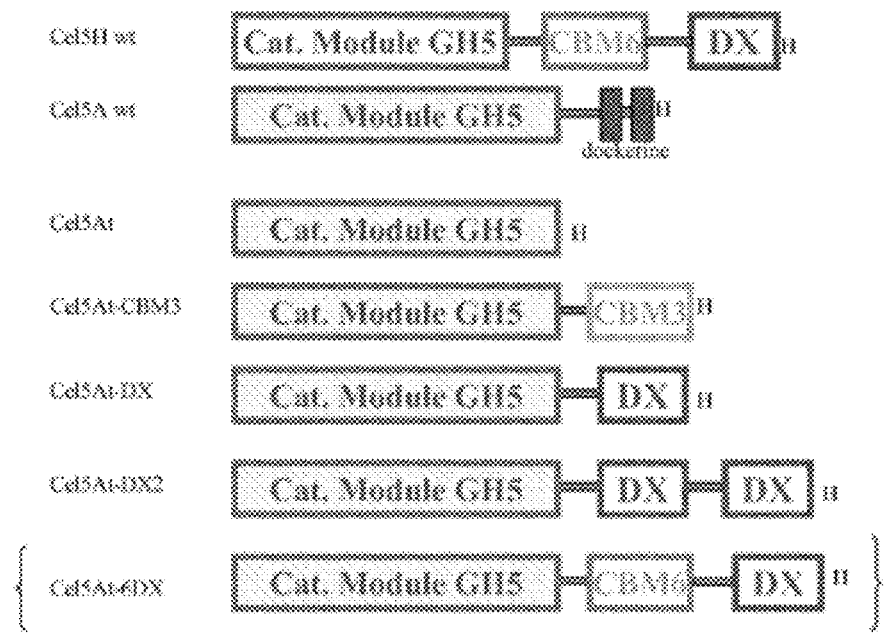
FIG. 7 illustrates schematic representation of engineered forms of Cel5A from *C. cellulolyticum* comprising added domains of Cel5H, according to particular embodiments of the invention. Legend: see FIG. 2.

The cellulase selected for these experiments was Cel5A from *C. cellulolyticum*, which analogously to Cel5H also displays a family-5 catalytic module at the N-terminus. Cel5A is a genuine endoglucanase with moderate activity on Avicel (Fierobe et al. 1991. J Bacteriol 173: 7956-62). The hybrid enzymes which were constructed are shown in FIG. 7.

Figure 8:
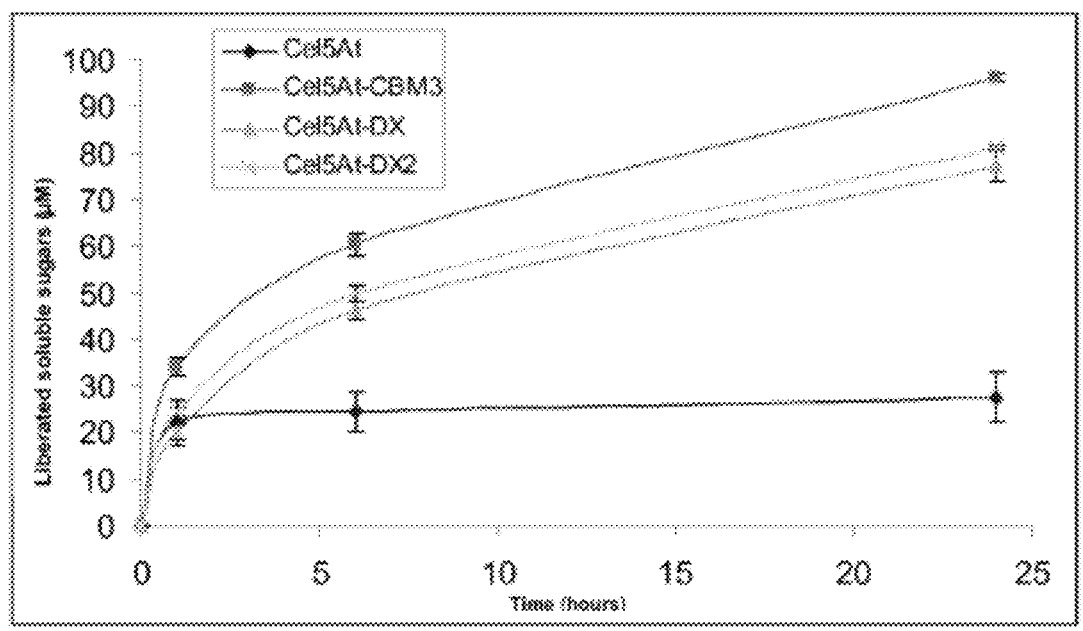
FIG. 8 illustrates the degradation of Avicel (3.5 g/L of 20 mM Tris-maleate pH 6 and 1 mM $CaCl_2$) by different engineered forms of Cel5A from *C. cellulolyticum* comprising added domains of Cel5H, according to particular embodiments of the invention. Legend: see FIG. 2.

The various engineered forms of Cel5A were purified and their activity was tested on Avicel and compared to Cel5Awt and Cel5At (FIG. 8). DZ The observed activity profiles indicated that the presence of a DZ domain ameliorates Cel5A activity (i.e. hydrolysis of Avicel by Cel5A). In particular, after 24 hours of incubation, the quantity of sugars liberated by Cel5At-DZ or Cel5At-DZ2 is three times higher than the quantity of sugars liberated by Cel5At. These results suggest that the enzyme is fixed or attached by the DZ domain onto the cellulose. Hence, it is suggested that the DZ domain is a new type of fixation domain.

However, the observed activities are 20% lower than the activity of Cel5At-CBM3. The scaffoldin CBM domain thus appears to be also relevant for the amelioration of Cel5A activity on crystalline cellulose.

The addition of two DZ domains does not significantly increase enzyme activity compared to enzyme constructs having only one DZ domain.

It is also noted that a Cel5A construct having one or more additional DZ domains, is still four times less active than wild type Cel5H cellulase on crystalline cellulose.

Therefore, a Cel5A construct, comprising both the CBM domain (CBM6) and the DZ domain from Cel5H is made. The introduction of a CBM6 domain in between the catalytic Cel5A domain and the Cel5H DZ domain increases enzyme activity with respect to the degradation of crystalline cellulose.

Example 6

Cel5H Activity is Complementary or Additive to the Activity of Other Cellulases on Crystalline Cellulose, in the Free State or Incorporated into a Hybrid Cellulosome Kinetic experiments were performed to investigate whether Cel5H activity is complementary or additive to that of other cellulase enzymes in the degradation of pure crystalline cellulose.

In these experiments, the following enzymes were tested:
wild type enzymes from *C. cellulolyticum*: Cel5A (endo), Cel9G (endo), Cel9M (endo), Cel9P (endo), Cel48F (processive) et Cel9E (processive).
Modified enzymes from *C. cellulolyticum*: Cip0-G (endo)
Enzymes isolated from organisms other than *C. cellulolyticum*: Cel6A (exo) de *Neocallimastix patriciarum* (mushroom).

The amount of soluble sugars that were liberated by the enzymes after 24 hours incubation on Avicel crystalline cellulose (3.5 g/L tampon, 20 mMTris-Maleate pH 6, 1 mM $CaCl_2$ 1) are shown in FIG. 9. For each combination of enzymes, the first bar indicates the sum of the individual activities of both enzymes, whereas the second bar indicates the activity of a mixture of both enzymes (each enzyme being present at a concentration of 0.1 mM).

These results indicate that the activities of other celluloses are in most cases complementary or additive to the activity of the Cel5H cellulose.

Figure 10:
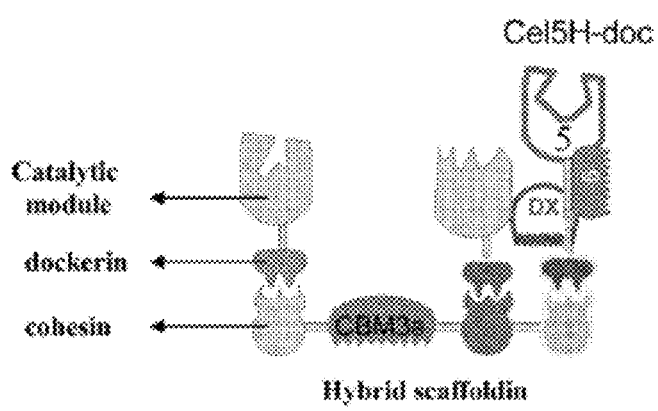
FIG. 10 schematically illustrates a hybrid minicellulosome including Cel5H, according to a particular embodiment of the invention.

Further experiments include the degradation of Avicel by hybrid minicellulosomes comprising Cel5H appended with a suitable dockerin module (such as, e.g., in FIG. 2), one or two other complementary cellulases bearing cognate dockerins and bound to a hybrid scaffoldin displaying an optional CBM3a module (see FIG. 10). Increased degradation of substrate compared to the Cel5H or other cellulases alone is demonstrated.

Example 7

Production and Secretion of Cel5H (Wild Type, Engineered, with Modified Signal Sequence) Alone or with Other Cellulases (and/or Scaffoldin) by *C. acetobutylicum*

The wild type gene encoding Cel5H was amplified by PCR from the strain *S. degradans*, and cloned in the *E. coli-C. acetobutylicum* pSOS952 shuttle vector. This plasmid is an expression vector for *C. acetobutylicum* (ferret et al. 2004. J Bacteriol 186: 253-7). The expression of the gene of interest is under the control of the strong and constitutive promoter (pthl) of the gene encoding the thiolase enzyme. Two lac operators were introduced upstream and downstream of the pthl to prevent any expression of the gene in *E. coli*. The vector was subsequently methylated (in vivo using the strain ER2275[pAN1] and in vitro using the methylase CpG) and used to electro-transform *C. acetobutylicum* strain as formerly described. Recombinant clones were obtained and PCR tests on colonies indicated that the vector remains intact in the solventogenic *Clostridium*. Several clones were grown in 2YTC medium, but no additional CMCase activity was detected in the culture supernatant compared to control strain harbouring the "empty" pSOS952 (CMCase test on plates).

Since the GC content of *S. degradans* is around 46%, whereas *C. acetobutylicum* displays a GC content of 31%, we predicted the wild-type gene encoding Cel5H may not be adapted to *C. acetobutylicum* codon bias. A synthetic gene encoding wild-type Cel5H but adapted to *C. acetobutylicum* codon bias was made and cloned as described above in pSOS952.

The codon optimised Cel5H coding sequence for *C. acetobutylicum* is shown in FIG. 1F (SEQ ID NO: 6) and the corresponding polypeptide sequence is shown in FIG. 1G (SEQ ID NO: 7). The sequences contain an engineered, C-terminal 6×His tag to facilitate detection and/or isolation.

Transformation of *C. acetobutylicum* with this new vector (after methylation) generated recombinant colonies. Analysis of the supernatant after growth in 2YTC revealed an improved CMCase activity, thus showing that active Cel5H was secreted by the recombinant strain. The secretion yield seems to presently remain below 1 mg/L.

S. degradans is a Gram-negative bacterium which displays two membranes (outer membrane and cytoplasmic membrane) whereas C. acetobutylicum (Gram-positive bacterium) only possesses a cytoplasmic membrane. The native signal sequence of Cel5H is thus designed to address secretion across two membranes but may not be suitable for efficient secretion by C. acetobutylicum. For this reason, using molecular biology techniques, we replaced the native signal sequence of Cel5H by that of Cel5A from C. cellulolyticum, since the latter is well secreted by C. acetobutylicum (up to 5 mg/L). We transformed C. acetobutylicum with the vector containing the hybrid gene. The secretion yield of Cel5H using the Cel5A signal sequence was investigated. It was shown that secretion levels were increased by the replacement of the native signal sequence of Cel5H by that of Cel5A from C. cellulolyticum. Due to the strong Cel5H activity on pNP-cellobioside, we were able to measure secretion levels of about 0.5 mg/L.

Figure 11:
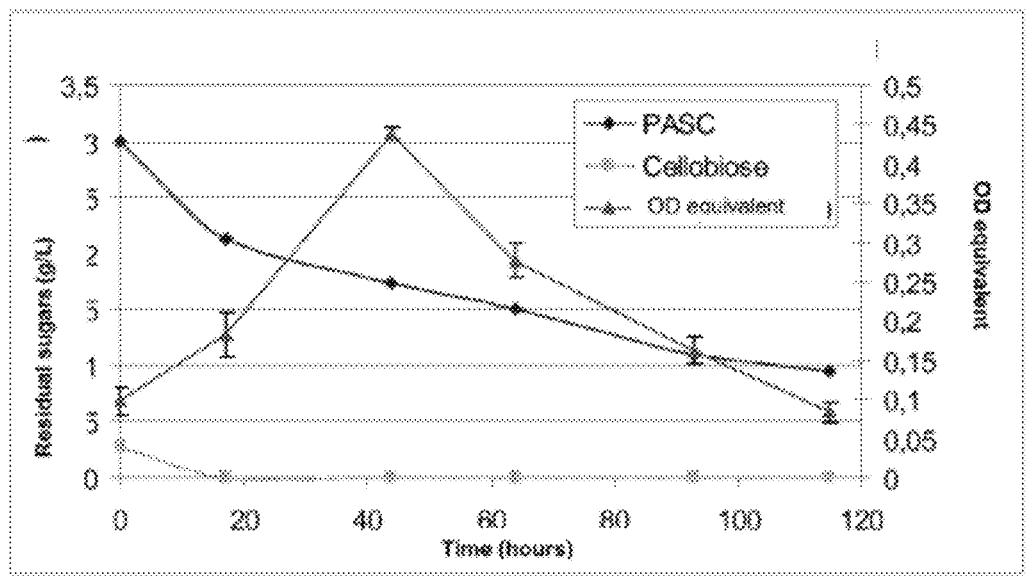
FIG. 11 shows the degradation of PASO, the consummation of residual cellobiose and the bacterial growth of *C. acetobutylicum*, having its Cel5H signal peptide sequence replaced by the Cel5H signal peptide sequence of *C. cellulolyticum* in a fermentor with 3 g/L 2YT-PASC and pH 5.5, according to particular embodiments of the invention.
Figure 12:
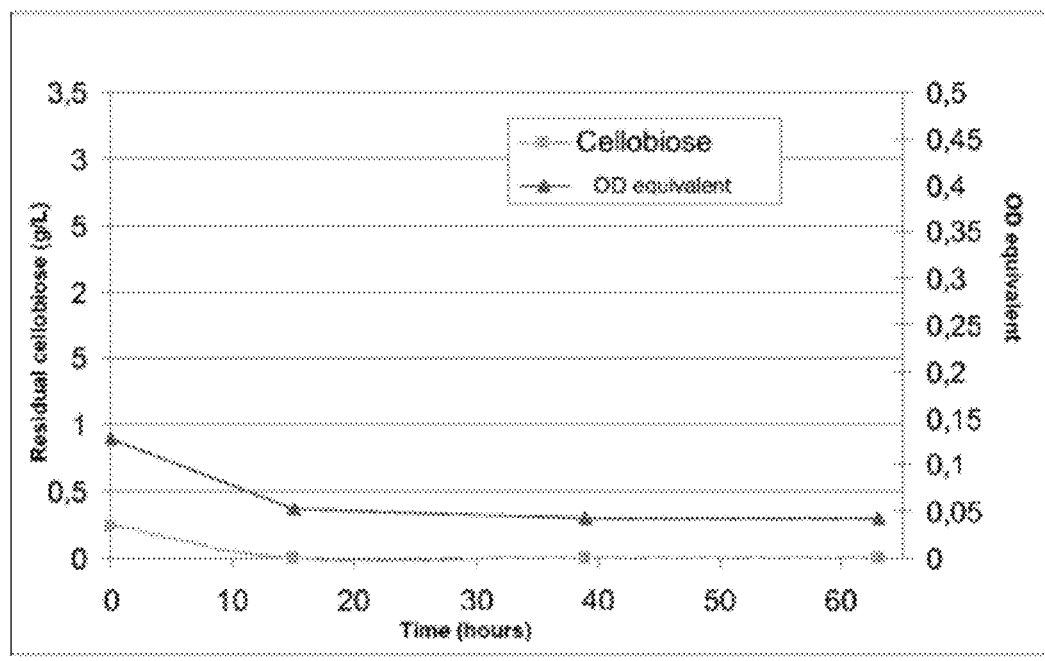
FIG. 12 shows the consummation of residual cellobiose and the bacterial growth of *C. acetobutylicum*, having its Cel5H signal peptide sequence replaced by the Cel5H signal peptide sequence of *C. cellulolyticum* in a fermentor in the presence of 2YT and pH 5.5 but without any PASO, according to particular embodiments of the invention.

A culture of the recombinant bacterial strain was grown in a fermentor in an environment of 3 g/L 2YT-PASC with a pH fixed at 5.5. We measured the degradation of PASO, the consummation of residual cellobiose and bacterial growth. The results are shown in FIGS. 11 and 12.

A significant bacterial growth was observed during the first 40 hours until an OD value of 0.45 was reached. Subsequently, cell lysis occurred. At the same time, an increasing degradation of PASO was observed. After 117 hours, 68% of the PASO was consumed but no mono- or oligosaccharides could be detected. This suggested that the sugars liberated by Cel5H by hydrolysis of PASO were immediately consumed by the bacteria. These results showed that we succeeded in constructing a strain which is capable of growing on PASO-supplemented medium.

A second culture of the recombinant bacterial strain was grown in a fermentor in an environment of 2YT (however not containing any PASO) with a pH fixed at 5.5. The goal of this experiment was to check the correlation between bacterial growth and the consummation of PASO. The results are shown in FIG. 12. As we expected, no bacterial growth could be observed in this case.

Therefore, we can conclude that the observed bacterial growth is due to the degradation of PASO and subsequent consumption of liberated sugars.

Furthermore, a third culture is set up, to check whether the observed bacterial growth is due to the activity of Cel5H and not to the activity of the endogenous enzymatic system of C. acetobutylicum. Therefore, a culture of a strain containing an empty vector (pSOS) is grown in a fermentor in an environment of 3 g/L 2YT-PASC with a pH fixed at 5.5.

Finally, a fourth culture is grown in a fermentor in an environment of 5 g/L 2YT-PASC with a pH fixed at 5.5 to check whether the PASO concentration is the limiting factor for bacterial growth. Thus, a higher concentration of PASO may potentially result in higher OD values (i.e. higher than the maximal OD value of 0.45 observed in the previous experiment).

The gene encoding Cel5H is cloned in combination with genes encoding other cellulases that act independently from Cel5H in the free state. Alternatively, the genes encoding efficient minicellulosomes comprising of Cel5H (appended with a dockerin), a scaffoldin and one or two other cellulase(s) bearing suitable dockerins are cloned and expressed in C. acetobutylicum.

When three or four different genes are cloned, a second expression vector called pMTL is also used. This vector was shown to be compatible with pSOS952 in C. acetobutylicum. Alternatively, the genes are integrated in the chromosome at specific sites (such as taught in inter alia patented PCT/EP/2006/066997), or randomly.

Moreover, cellulases with added modules of Cel5H (particularly DZ and optionally CBM6, see Example 4) are cloned and expressed in C. acetobutylicum, to achieve an increased degradation and utilisation of crystalline cellulose.

We use both wild-type and various engineered strains of C. acetobutylicum, such as for example strains with modified secretion machinery, optimised for the secretion of heterologous proteins, and/or modified metabolism for optimised production of ethanol (or butanol).

The corresponding recombinant C. acetobutylicum are shown to produce and secrete the engineered enzymes, and display ability to grow on and/or degrade one or more cellulosic substrates.

Example 8

Improvement of the Secretion of cel5H by C. acetobutylicum

Figure 13:
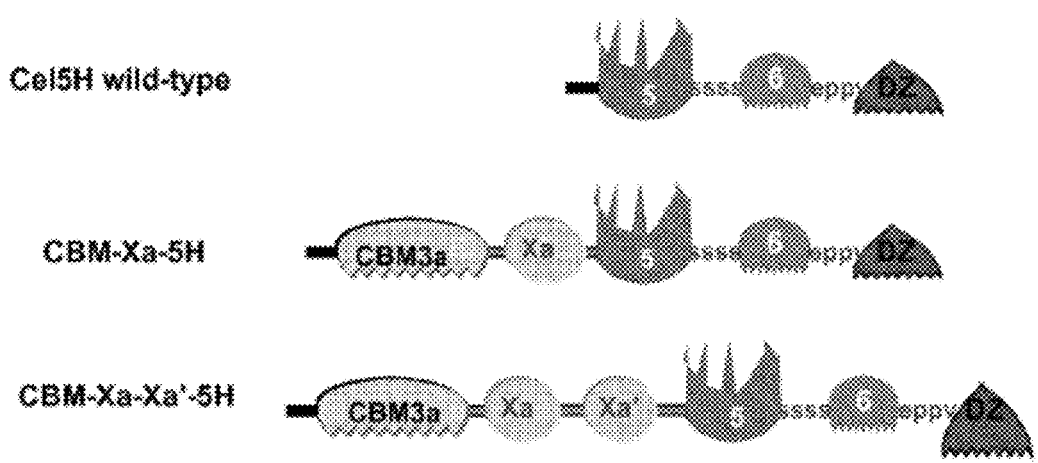
FIG. 13 is a schematic representation of different constructs according to particular embodiments of the invention. The constructs comprise a polypeptide of interest (cellulase "Cel5H") fused to a carrier domain and a signal sequence. The carrier domain comprises a carbohydrate binding module (CBM3a) from a cellulosomal scaffolding protein fused to one or two X modules (Xa). Cellulase Cel5H comprises a glycoside hydrolase family 5 domain ("5"), a polyserine linker ("sss"), a carbohydrate-binding module family 6 domain ("6"), a glutamic acid-proline-rich region ("eppv") and a C-terminal domain identified by the present inventors as a putative carbohydrate-binding module ("DZ").

Various constructions were made and are schematically represented on FIG. 13, wherein modules obtained from different scaffolding proteins were used.

In a first construct, the synthetic polynucleic acid adapted to C. acetobutylicum codon bias and encoding the cellulase Cel5H from Saccharophagus degradans, was fused to a polynucleic acid encoding a carrier domain and comprising the CBM3a module, the first (Xa) and the second (Xa') X modules obtained from the CipA protein of C. acetobutylicum and the signal peptide of the CipC scaffolding protein of C. cellulolyticum. Suitable linker sequences are used to link the different modules to one another.

The domain structure of the native Cel5H polypeptide can be outlined as GH5-PSL-CBM6-EPR-DZ, wherein GH5 stands for its glycoside hydrolase family 5 domain, PSL for the polyserine linker, CBM6 for carbohydrate-binding module family 6 domain, EPR for the glutamic acid-proline-rich region and, without being limited to this interpretation, DZ represents a C-terminal domain identified by the present inventors as a putative carbohydrate-binding module.

This construct was constructed using Overlap Extension PCR technique, and cloned in the shuttle expression vector pSOS952, that confers resistance to the antibiotic erythromycin, thereby generating the plasmid pSOS952-CBM-Xa-Xa'-5H. The constructs were checked by sequencing, and methylated in vivo and in vitro. The methylated vector was subsequently used to electrotransform C. acetobutylicum strain ATTC 824.

Figure 14:
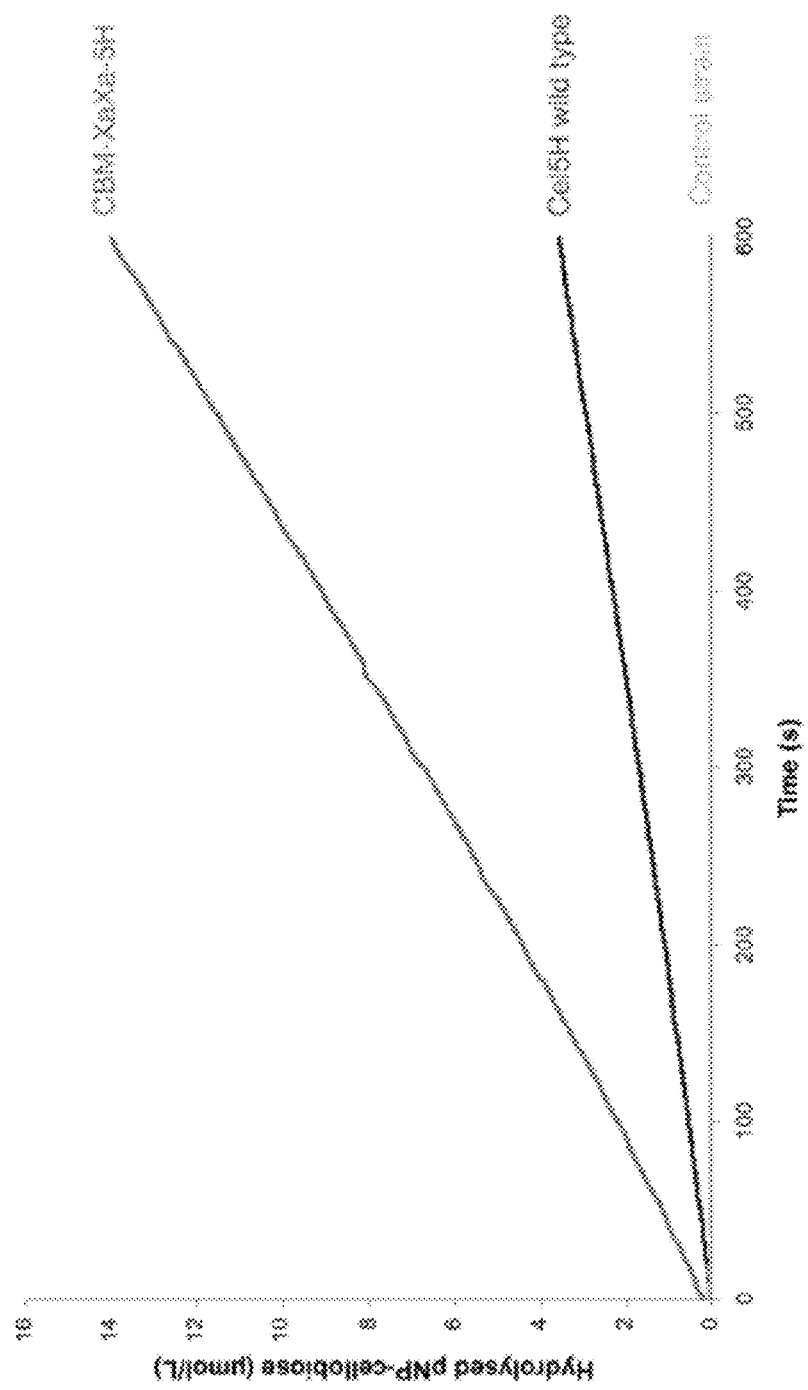
FIG. 14 demonstrates the secretion of wild-type Cel5H and Cel5H fused to a carrier domain, compared to a control strain. The carrier domain encompasses a carbohydrate binding module (CBM3a) from a cellulosomal scaffolding protein fused to two hydrophilic domains (Xa). The activity of the culture supernatant was measured on the soluble substrate para-nitrophenyl-cellobiose.

The secretion by C. acetobutylicum of the wild-type Cel5H protein appended with the signal peptide of the scaffoldin CipC from C. cellulolyticum was 0.5-0.9 mg/L (values based on the activity of the culture supernatant on para-nitrophenyl-cellobioside). However, C. acetobutylicum strains bearing the two constructs encoding the fusion protein comprising the Cel5H protein linked to the carrier domain secreted a fusion protein containing the cellulase 5H in their growth medium in significantly higher amounts, more particularly up to 6.1 mg/L (value based on the activity of the culture supernatant on para-nitrophenyl-Cellobioside, see FIG. 14(3). These results demonstrate the production and secretion of Cel5H by C. acetobutylicum.

Example 9

Demonstration of the Activity of the Fusion Proteins According to the Invention on Cellulose Using molecular biology techniques the DNA encoding the different protein constructs described in Example 8 was amplified and cloned in an *E. coli* expression vector (pET22b (+), Novagen). The resulting vector was used to transform the *E. coli* strain BL21 (DE3) (Novagen). In all cases, six H is codons were grafted at the C-terminus extremity of the recombinant proteins to facilitate their purification on Nickel resin (Ni-NTA, Qiagen).

The recombinant strains were grown in Luria Bertani medium and the expression of the cloned genes was triggered using IPTG as the inducer. The synthesis of the recombinant proteins was verified by denaturing polyacrylamide gel electrophoresis (SDS-PAGE). The cultures were centrifuged and the harvested cells were broken in a French press.

The recombinant proteins were purified by loading the crude extract on Ni-NTA (Qiagen), and elution of the protein of interest using increasing concentrations of imidazolium. Purification was achieved using FPLC Q-sepharose (Hitrap Q HP resin, GE Healthcare).

Figure 15A:
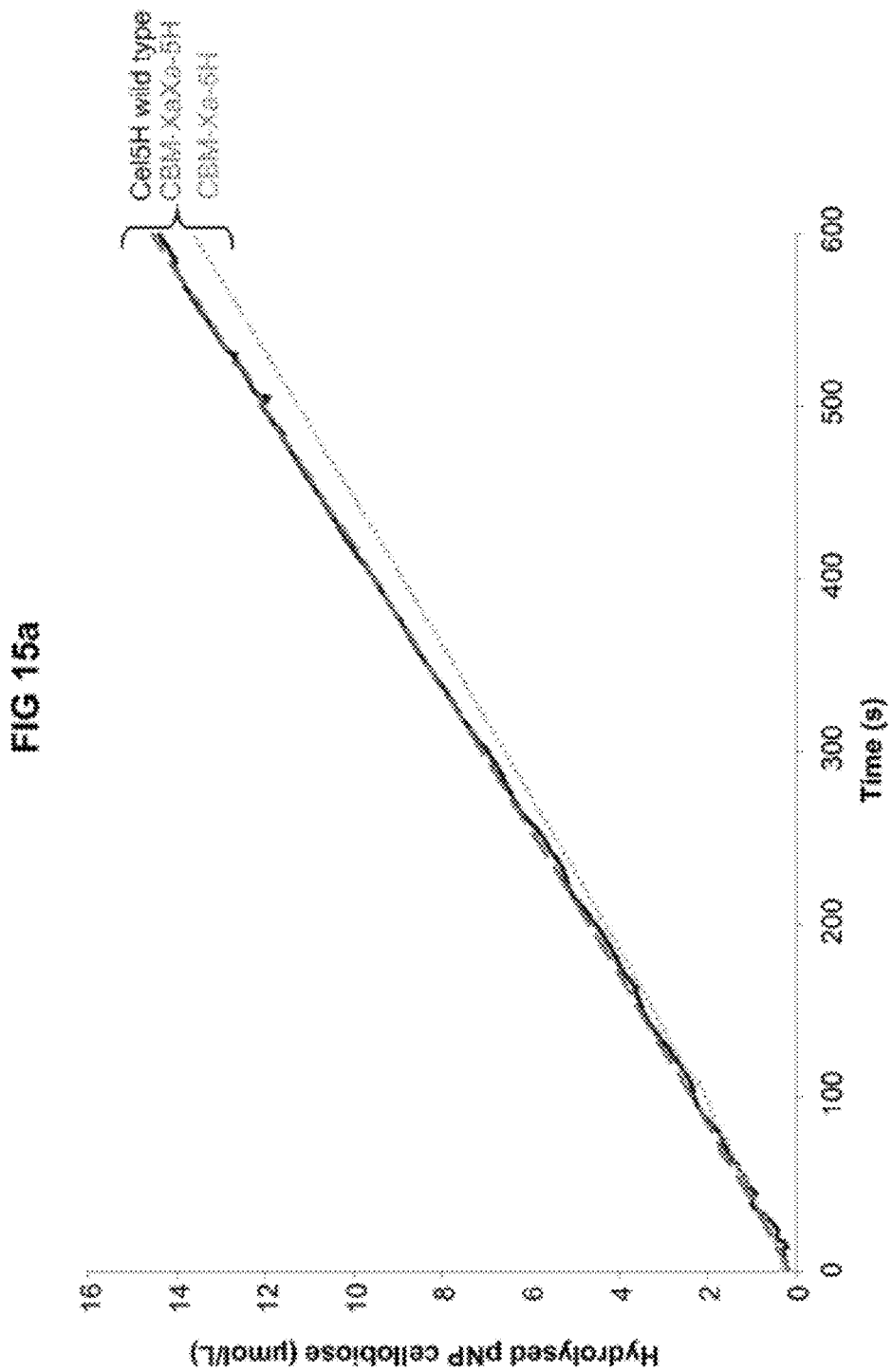
FIG. 15 demonstrates the activity of different proteins including the fusion proteins according to particular embodiments of the invention on different celluloic substrates; (a) activity of proteins comprising Cel5H on soluble substrate para-nitrophenyl-cellobiose; wild-type Cel5H (full line), fusion with one X module (CBM-Xa-5H; dotted line), fusion protein with two X modules (CBM-Xa-Xa-5H, dashed line) (b) activity of proteins comprising cel5H on crystalline cellulose Avicel.
Figure 15B:
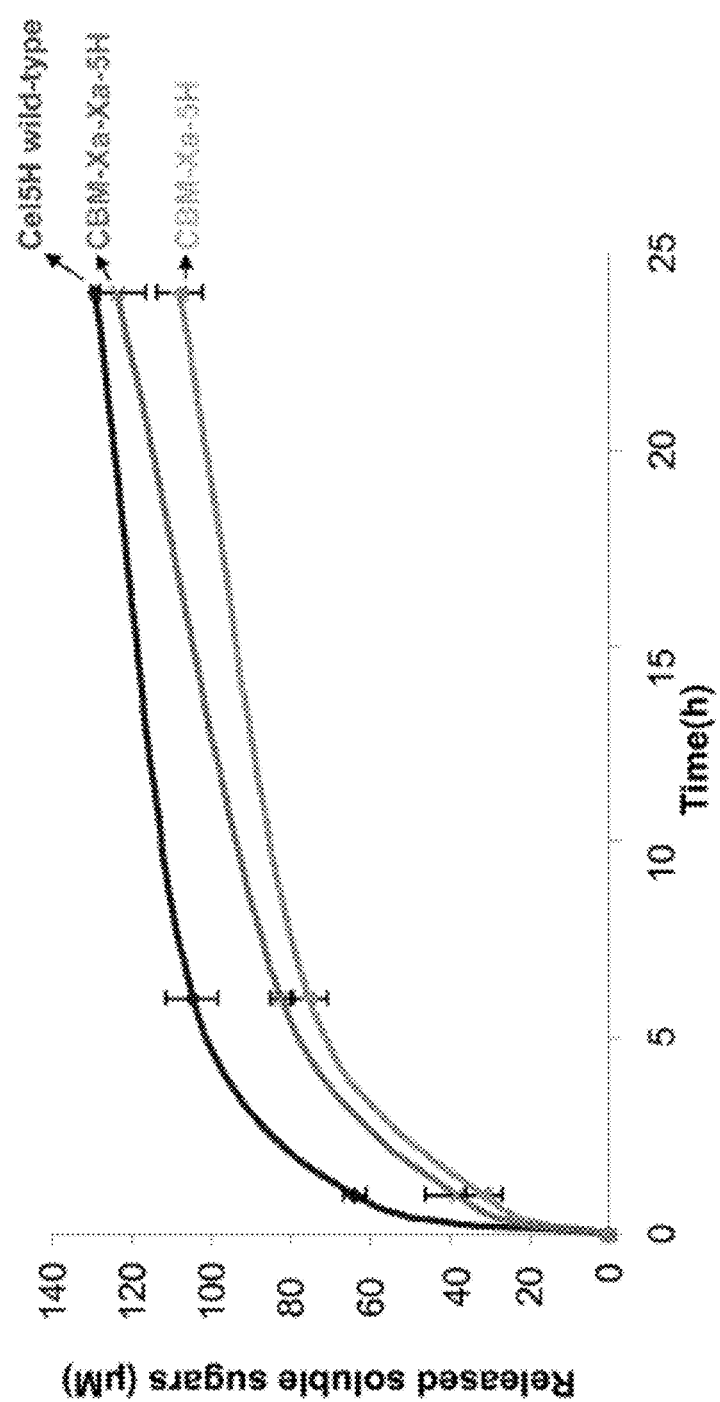

Activity of the purified cel5H enzyme was tested on para-nitrophenyl-cellobioside and the results are presented in FIG. 15a. Alternatively, the activity was measured on Avicel (microcrystalline cellulose) using standard conditions (37° C.). The results are illustrated in FIG. 15b.

Example 10

The Cloning and Expression Strategies as Described in Examples 2 to 7 are Used with Cel5H Homologues, Particularly with ACLA from *Pseudomonas* sp ND137 Encoded by the Gene aclA The same strategy is applied with enzymes which display an important overall homology with Cel5H from *S. degradans*, and in particular possess a DZ domain.

Figure 16:
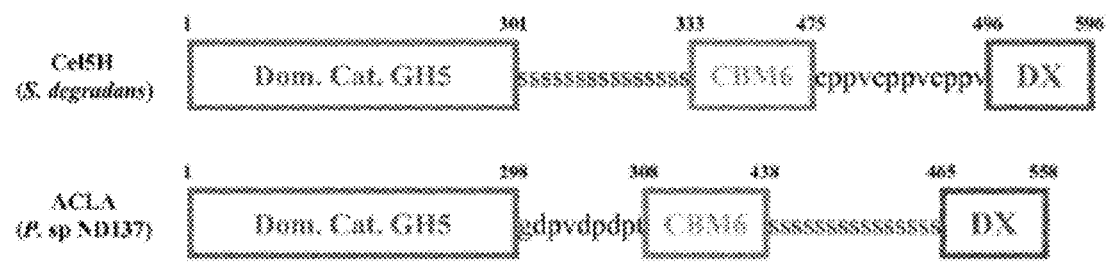
FIG. 16 schematically illustrates comparison of domains of Cel5H and ACLA, according to particular embodiments of the invention.

This is exemplified by the enzyme (ACLA) encoded by the gene ac/A from *Pseudomonas* sp ND137. FIG. 16 compares the general organisation of ACLA with that of Cel5H. The gene encoding ACLA has already been cloned and overexpressed in *E. coli*, but the corresponding enzyme was not fully characterized (Aoki & Kamei 2006. European Journal of Phycology 41: 321-328).

With respect to the high degree of homology between these two enzymes (with the exception of the linkers), they are expected to share similar properties/activities. Consequently, the cloning and expression strategies described in Examples 2 to 7 are applied to ACLA, and producing a further cellulose-degrading system particularly in *C. acetobutylicum*.

Example 11

Evaluation of the Activity of ACLA on Various Substrates Including Para-nitrophenyl-β-D-Cellobioside (pNPC), Phosphoric Acid-Swollen Cellulose (PASC) and Avicel Activity of the purified ACLA enzyme was tested on a variety of substrates using standard conditions (37° C.) and compared to the activity of purified recombinant Cel5H on the same substrates.

The enzymatic activity of ACLA was tested on the soluble chromogenic substrate, para-nitrophenyl-β-D-cellobioside (pNPC) and compared to that of Cel5H (at 95% purity). Upon cleavage by the enzyme of the link between the para-nitrophenyl group and the cellobiose, para-nitrophenol and cellobiose is liberated and its concentration can be directly determined by means of spectrophotometric analysis. The enzymatic activity of ACLA on para-nitrophenyl-β-D-cellobioside was 17.9 ui/µmol, whereas the enzymatic activity of Cel5H on the same substrate was 18.2 ui/µmol. Accordingly, ACLA showed 98% of enzymatic activity compared to Cel5H on para-nitrophenyl-β-D-cellobioside substrate.

For testing of activity on PASC (amorphous cellulose), the enzyme concentration used was 5 nM and the substrate concentration was at 3.5 g/L (pH 6.0). The enzymatic activity of ACLA on PASC was 780 ui/µmol, whereas the enzymatic activity of Cel5H on the same substrate was 1600 ui/µmol. Accordingly, ACLA showed 49% of enzymatic activity compared to Cel5H on PASC.

For testing of activity on Avicel (crystalline cellulose), the enzyme concentration is 100 nM and substrate is at 3.5 g/L (pH 6.0). The enzymatic activity of ACLA on Avicel was 56 µM/24 h, whereas the enzymatic activity of Cel5H on the same substrate was 140 µM/24 h. Accordingly, ACLA showed 40% of enzymatic activity compared to Cel5H on Avicel.

---

The invention claimed is:

1. A recombinant *Clostridium* bacterium transformed with and expressing the Cel5H polypeptide of *Saccharophagus degradans* strain 2-40 or a homologue thereof having at least 95% sequence identity with said Cel5H polypeptide of *Saccharophagus degradans* strain 2-40, wherein said recombinant bacterium is capable of secreting said Cel5H polypeptide and capable of degrading cellulose.

2. The recombinant bacterium according to claim 1 comprising a recombinant nucleic acid molecule encoding said Cel5H polypeptide of *Saccharophagus degradans* strain 2-40 or said homologue having at least 95% sequence identity with said Cel5H polypeptide of *Saccharophagus degradans* strain 2-40, operably linked to regulatory sequences which allow for expression in said microorganism.

3. The recombinant bacterium according to claim 1, which is a solventogenic bacterium.

4. The recombinant bacterium according to claim 1, which is *Clostridium acetobutylicum*.

5. The recombinant bacterium according to claim 1, wherein said Cel5H polypeptide of *Saccharophagus degradans* strain 2-40 or said homologue having at least 95% sequence identity with said Cel5H polypeptide of *Saccharophagus degradans*, is fused to a glycoside hydrolase (GH) catalytic domain, a carbohydrate-binding module (CBM) domain, a cohesin-binding domain, or a hydrophilic (X module) domain of a cellulosomal scaffoldin protein.

6. The recombinant bacterium according to claim 1, wherein said Cel5H polypeptide of *Saccharophagus degradans* strain 2-40 or said homologue thereof, and optionally the one or more enzymes capable of degrading a substance comprising cellulose, are comprised in a covalent cellulosome.

7. A method for the degradation of a substance comprising cellulose, wherein said method comprises contacting said substance with the recombinant *Clostridium* bacterium according to claim 1, growing said recombinant bacterium on said substance comprising or enriched in crystalline or semi-crystalline cellulose and ensuring direct production of the degraded cellulose comprising substance.

8. A method for producing a solvent, fuel or chemical intermediate from a substance comprising cellulose, wherein said method comprises treating said substance with the recombinant microorganism of the genus *Clostridium* according to claim 1, growing said recombinant microorganism on said substance comprising or enriched in crystalline or semi-crystalline cellulose, and ensuring direct production of said solvent, fuel or chemical intermediate from said substance comprising cellulose.

9. The method according to claim 7, wherein said substance comprises or is enriched in crystalline cellulose.

10. The method according to claim 8, wherein said substance comprises or is enriched in crystalline cellulose.

11. The recombinant bacterium according to claim 3, wherein the solventogenic bacterium is an ethanologenic bacterium.

12. The recombinant bacterium according to claim 1, wherein said Cel5H polypeptide of *Saccharophagus degradans* strain 2-40, or a homologue thereof, comprises one or more domains chosen from or corresponding to the GH5 domain, the CBM6 domain, or the DZ domain of Cel5H.

13. The method according to claim 7, wherein the method is performed at less than 50° C.

14. The method according to claim 8, wherein the method is performed at less than 50° C.

* * * * *

UNITED STATES PATENT AND TRADEMARK OFFICE
CERTIFICATE OF CORRECTION

PATENT NO. : 8,871,479 B2
APPLICATION NO. : 13/131478
DATED : October 28, 2014
INVENTOR(S) : Fierobe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 83 days.

Signed and Sealed this
Sixth Day of June, 2017

Michelle K. Lee
*Director of the United States Patent and Trademark Office*